US010850176B2

(12) United States Patent
Oguchi et al.

(10) Patent No.: US 10,850,176 B2
(45) Date of Patent: Dec. 1, 2020

(54) SENSOR DEVICE

(71) Applicant: SONY CORPORATION, Tokyo (JP)

(72) Inventors: Yoshio Oguchi, Kanagawa (JP);
Toshiki Hashida, Kanagawa (JP);
Kosei Yamashita, Kanagawa (JP);
Hideyuki Matsunaga, Kanagawa (JP);
Shinji Yamamura, Chiba (JP);
Tatsuhiro Obara, Chiba (JP)

(73) Assignee: SONY CORPORATION, Tokyo (JP)

( * ) Notice: Subject to any disclaimer, the term of this patent is extended or adjusted under 35 U.S.C. 154(b) by 255 days.

(21) Appl. No.: 14/786,343

(22) PCT Filed: Dec. 6, 2013

(86) PCT No.: PCT/JP2013/082886
§ 371 (c)(1),
(2) Date: Oct. 22, 2015

(87) PCT Pub. No.: WO2014/178154
PCT Pub. Date: Nov. 6, 2014

(65) Prior Publication Data
US 2016/0089085 A1    Mar. 31, 2016

(30) Foreign Application Priority Data

Apr. 30, 2013 (JP) ................................ 2013-095689
Jul. 17, 2013 (JP) ................................ 2013-148533

(51) Int. Cl.
*A63B 60/46* (2015.01)
*A63B 69/36* (2006.01)
(Continued)

(52) U.S. Cl.
CPC ............ *A63B 60/46* (2015.10); *A61B 5/6895* (2013.01); *A63B 24/0003* (2013.01);
(Continued)

(58) Field of Classification Search
CPC ............ A61B 5/6895; A61B 2090/064; A61B 2503/10; A61B 2505/09;
(Continued)

(56) References Cited

U.S. PATENT DOCUMENTS 3,717,857 A * 2/1973 Evans .................. A61B 5/1107
340/870.13
4,991,850 A * 2/1991 Wilhlem ............ A63B 69/3632
473/233
(Continued)

FOREIGN PATENT DOCUMENTS

FR    2829700 A1 *  3/2003 ......... A63B 69/3632
FR    2829700 A1    3/2003
(Continued)

OTHER PUBLICATIONS

Nov. 18, 2016, EP communication issued for related EP application No. 13883787.7.
(Continued)

*Primary Examiner* — Marrit Eyassu
(74) *Attorney, Agent, or Firm* — Paratus Law Group, PLLC

(57) ABSTRACT

To detect a motion of a hitting tool more precisely by a sensor, provided is a sensor device including: a base member configured to be mounted on a hitting tool via a fitting structure; a substrate joined to the base member; a sensor disposed on the substrate and configured to detect a motion of the hitting tool delivered via the base member and the substrate; a communication unit configured to transmit a detection result of the motion of the hitting tool to an external device; and an exterior member configured to cover the sensor and the communication unit.

12 Claims, 42 Drawing Sheets

(51) Int. Cl.
*A63B 24/00* (2006.01)
*A61B 5/00* (2006.01)
*G01C 19/00* (2013.01)
*G01P 15/02* (2013.01)
*A63B 102/18* (2015.01)
*A63B 102/04* (2015.01)
*A63B 102/02* (2015.01)
*A63B 102/32* (2015.01)
*A61B 90/00* (2016.01)

(52) U.S. Cl.
CPC .......... *A63B 69/3632* (2013.01); *G01C 19/00* (2013.01); *G01P 15/02* (2013.01); *A61B 2090/064* (2016.02); *A61B 2503/10* (2013.01); *A61B 2505/09* (2013.01); *A61B 2560/0214* (2013.01); *A63B 2102/02* (2015.10); *A63B 2102/04* (2015.10); *A63B 2102/18* (2015.10); *A63B 2102/32* (2015.10); *A63B 2220/803* (2013.01); *A63B 2220/833* (2013.01); *A63B 2225/50* (2013.01)

(58) Field of Classification Search
CPC ........ A61B 2560/0214; A63B 24/0003; A63B 49/08; A63B 69/3632; A63B 2102/02; A63B 2102/04; A63B 2102/18; A63B 2102/32; A63B 2220/803; A63B 2220/833; A63B 2225/50; G01C 19/00; G01P 15/02
USPC ........................................................ 73/12.04
See application file for complete search history.

(56) References Cited

U.S. PATENT DOCUMENTS

| | | | | |
|---|---|---|---|---|
| 5,056,783 A * | 10/1991 | Matcovich | ......... | A63B 69/0024 473/453 |
| 5,688,183 A * | 11/1997 | Sabatino | ............ | A41D 19/0027 473/209 |
| 5,779,555 A * | 7/1998 | Nomura | ............. | A63B 69/3632 473/223 |
| 6,173,610 B1 * | 1/2001 | Pace | .................. | A63B 69/0002 73/493 |
| 8,672,779 B1 * | 3/2014 | Sakyo | ................ | A63B 24/0006 473/223 |
| 9,381,415 B1 * | 7/2016 | DiGregorio | ........ | A63B 24/0075 |
| 2006/0052173 A1 * | 3/2006 | Telford | ............. | A63B 24/0003 473/131 |
| 2006/0084516 A1 * | 4/2006 | Eyestone | ........... | A63B 69/3632 473/219 |
| 2008/0115582 A1 * | 5/2008 | Sato | .................... | A63B 69/3632 73/649 |
| 2008/0254907 A1 * | 10/2008 | Swartz | ............... | A63B 69/3617 473/237 |
| 2010/0248852 A1 * | 9/2010 | Lee | ......... | A63B 15/02 473/220 |
| 2011/0130227 A1 * | 6/2011 | Chen | .................. | A63B 69/0071 473/450 |
| 2012/0052973 A1 * | 3/2012 | Bentley | .................. | A63B 60/16 473/223 |
| 2012/0277015 A1 | 11/2012 | Boyd et al. | | |
| 2012/0296454 A1 | 11/2012 | Lui et al. | | |
| 2013/0065703 A1 | 3/2013 | Rose | | |
| 2013/0203518 A1 * | 8/2013 | Hatton | ................ | A63B 53/047 473/223 |

FOREIGN PATENT DOCUMENTS

| | | |
|---|---|---|
| JP | 2008-529727 | 8/2008 |
| JP | 2009-240677 | 10/2009 |
| JP | 2012-157644 | 8/2012 |
| JP | 2013-195103 | 9/2013 |
| WO | WO 03/089940 A1 | 10/2003 |
| WO | WO2006/010934 A1 | 2/2006 |
| WO | WO2011/085494 A2 | 7/2011 |

OTHER PUBLICATIONS

Mar. 27, 2019, European Communication issued for related EP Application No. 13883787.7.

\* cited by examiner

FIG.6
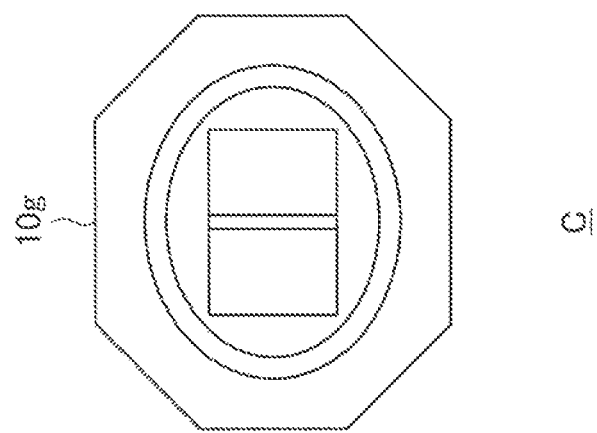
C
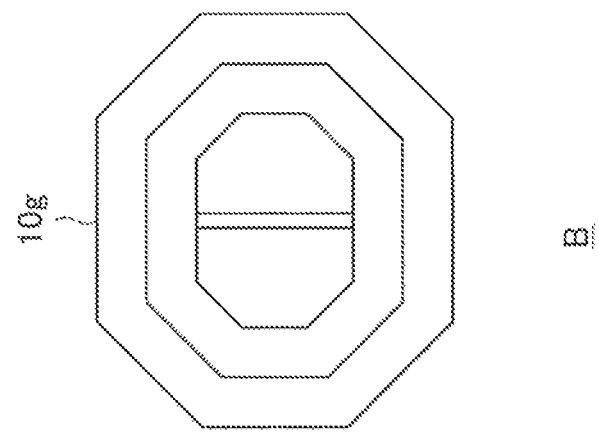
B
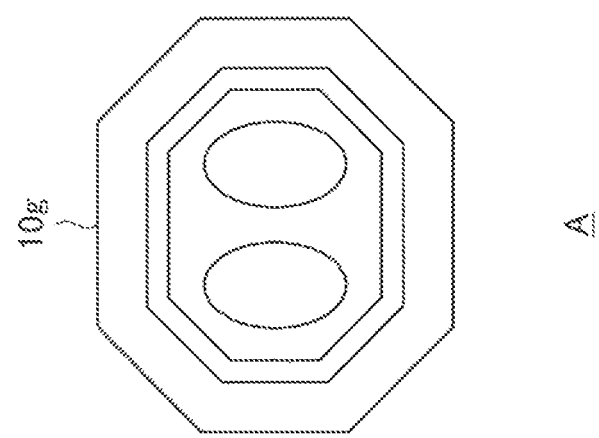
A

FIG.32
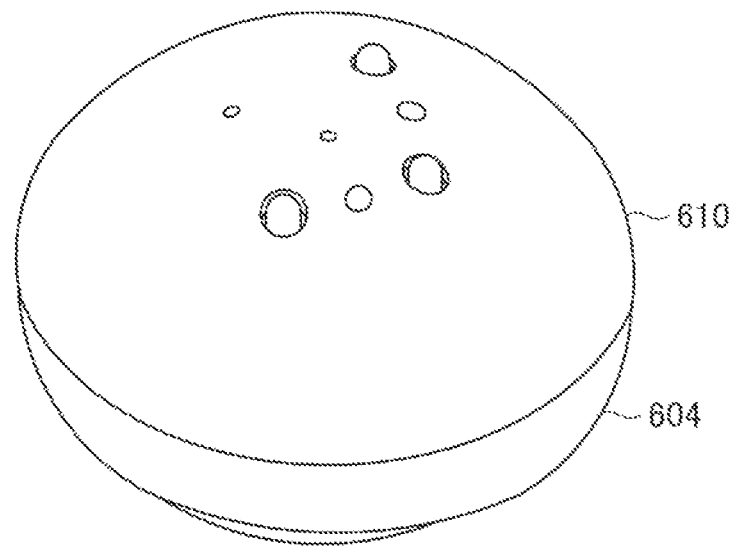
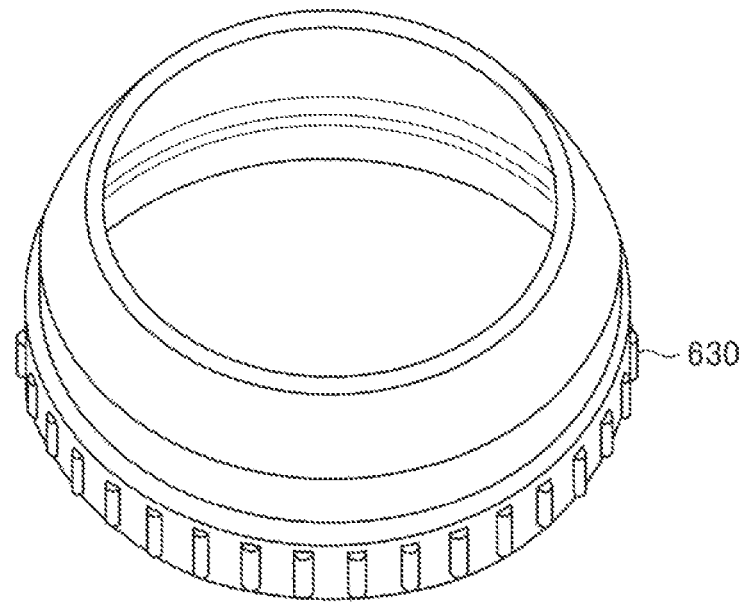

FIG.34
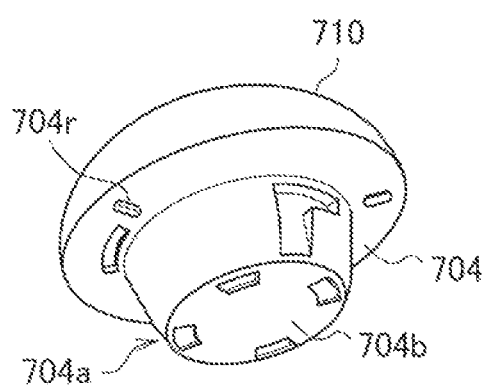
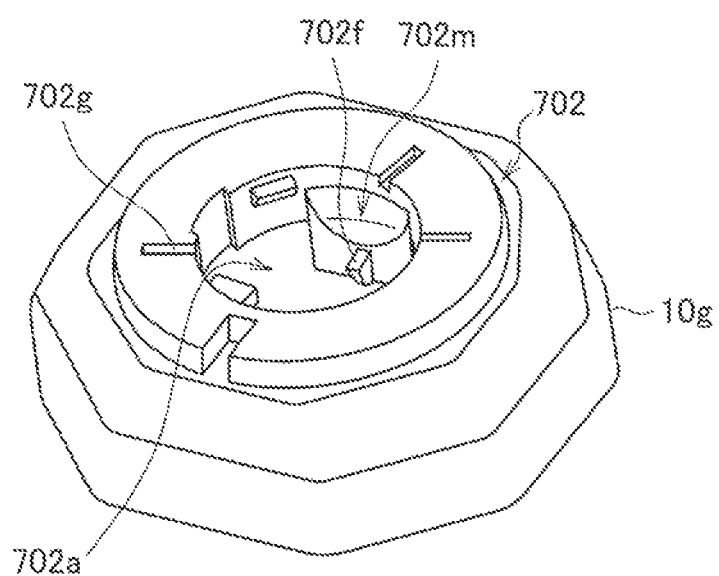

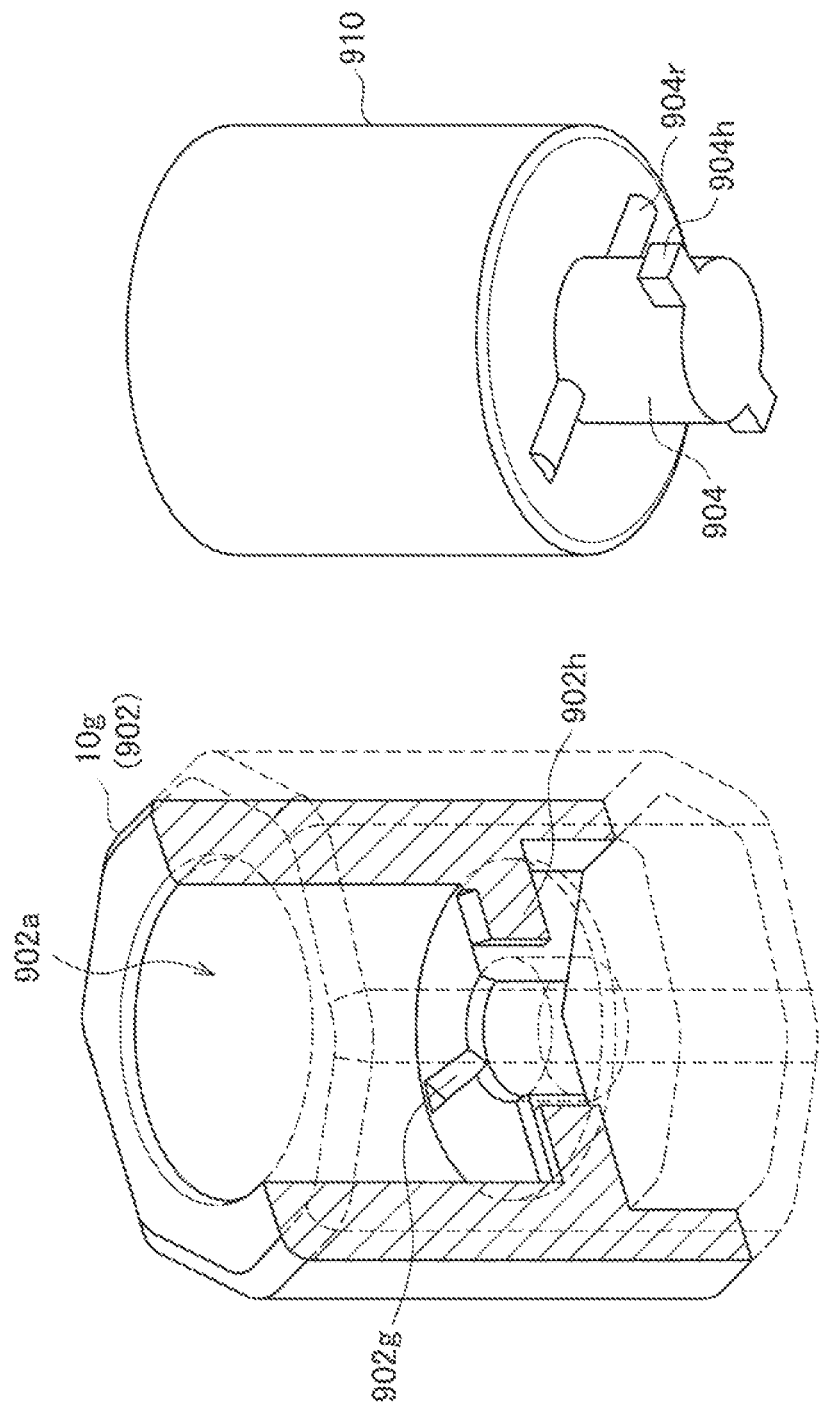

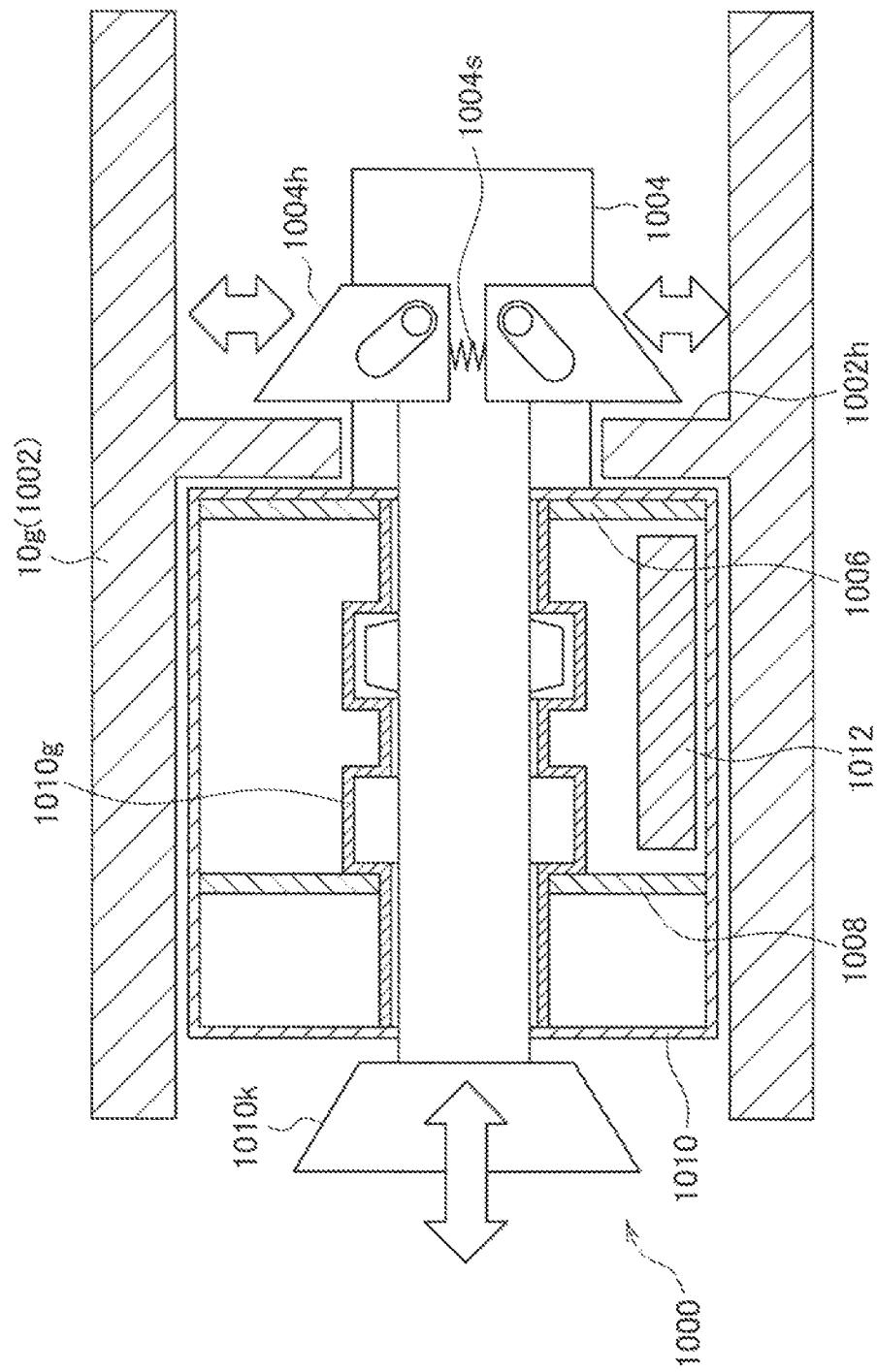

SENSOR DEVICE

CROSS REFERENCE TO PRIOR APPLICATION

This application is a National Stage Patent Application of PCT International Patent Application No. PCT/JP2013/082886 (filed on Dec. 6, 2013) under 35 U.S.C. § 371, which claims priority to Japanese Patent Application Nos. 2013-148533 (filed on Jul. 17, 2013) and 2013-095689 (filed on Apr. 30, 2013), which are all hereby incorporated by reference in their entirety.

TECHNICAL FIELD

The present disclosure relates to a sensor device fitted on a hitting tool.

BACKGROUND ART

Many technologies for assist users with improvement in sports using sensing or analysis have been developed already. For example, Patent Literature 1 describes a technology for extracting feature information of a swing by analyzing a detection result supplied by a sensor device including an angular velocity sensor or an acceleration sensor fitted on a hitting tool such as a golf club used by a user.

CITATION LIST

Patent Literature

Patent Literature 1: JP 2012-157644A

SUMMARY OF INVENTION

Technical Problem

In the above-described technology, since it is necessary for the sensor to precisely detect a motion of the hitting tool, the way in which the sensor device is fitted on the hitting tool is important. However, it is hard to say that the structure of the sensor device including a portion fitted on the hitting tool has been sufficiently proposed in, for example, Patent Literature 1 described above.

Accordingly, it is desirable to provide a novel and improved sensor device in which a motion of a hitting tool can be detected more precisely by a sensor.

Solution to Problem

According to the present disclosure, there is provided a sensor device including: a base member configured to be mounted on a hitting tool via a fitting structure; a substrate joined to the base member, a sensor disposed on the substrate and configured to detect a motion of the hitting tool delivered via the base member and the substrate; a communication unit configured to transmit a detection result of the motion of the hitting tool to an external device; and an exterior member configured to cover the sensor and the communication unit.

When the base member is fitted on the hitting tool via a fitting structure, the base member is fitted so that a motion of the hitting tool is delivered to the sensor via the base member, and thus the motion of the hitting tool can be detected more precisely by the sensor.

Advantageous Effects of Invention

According to an embodiment of the present disclosure described above, a motion of a hitting tool can be detected more precisely by a sensor.

BRIEF DESCRIPTION OF DRAWINGS

FIG. 6 is a diagram illustrating several examples of the shape of a grip end when a cap is removed.

FIG. 32 is an explanatory diagram illustrating a schematic configuration of the sensor device according to the sixth embodiment of the present disclosure.

FIG. 34 is an explanatory diagram illustrating a schematic configuration of a sensor device according to a seventh embodiment of the present disclosure.

FIG. 41 is an explanatory diagram illustrating a junction structure between a fitting structure and a base member of the sensor device according to the ninth embodiment of the present disclosure.

FIG. 42 is a sectional view illustrating a schematic configuration of a sensor device and a grip end according to a tenth embodiment of the present disclosure.

DESCRIPTION OF EMBODIMENTS

Hereinafter, preferred embodiments of the present disclosure will be described in detail with reference to the appended drawings. Note that, in this specification and the drawings, elements that have substantially the same function and structure are denoted with the same reference signs, and repeated explanation is omitted.

The description will be made in the following order.
1. First Embodiment
1-1. Overall configuration
1-2. First example of junction structure
1-3. Second example of junction structure
1-4. Third example of junction structure
1-5. Example of charger connection
2. Second Embodiment
3. Third Embodiment
4. Fourth Embodiment
5. Fifth Embodiment
6. Sixth Embodiment
7. Seventh Embodiment
8. Eighth Embodiment
9. Ninth Embodiment
10. Tenth Embodiment
11. Supplement

INTRODUCTION

Since a user has a plurality of hitting tools in sports plays in many cases, a sensor device preferably has an easily detachably mounted structure. Such easy detaching and mounting is also necessary at the time of charging or software update. On the other hand, when a ball is hit with a hitting tool or the hitting tool falls, impact acceleration of hundreds of G to thousands of G is applied to the sensor device depending on a case. Even in this case, it is necessary to closely stick the sensor device to a hitting tool so that the sensor device does not come off of the hitting tool or fitting of the sensor device does not become loose. Simultaneously, it is necessary to provide a mechanism delivering a minute vibration component (equal to or less than 1 G) occurring in a hitting tool to a sensor circuit without attenuation while protecting a sensor circuit against destruction or looseness caused due to the above impact. It is difficult to realize a mechanism capable of sensing even minute vibration equal to or less than only 1 G simultaneously while protecting a sensor circuit from an impact of thousands of G and capable of being easily detachably mounted.

Accordingly, in several embodiments to be described below, fitting mechanisms that are fitted on hitting tools with any shape and that acquire vibration of a hitting tool with high precision and simultaneously protect contents against an external impact will be proposed.

1. First Embodiment (1-1. Overall Configuration)

Figure 1:
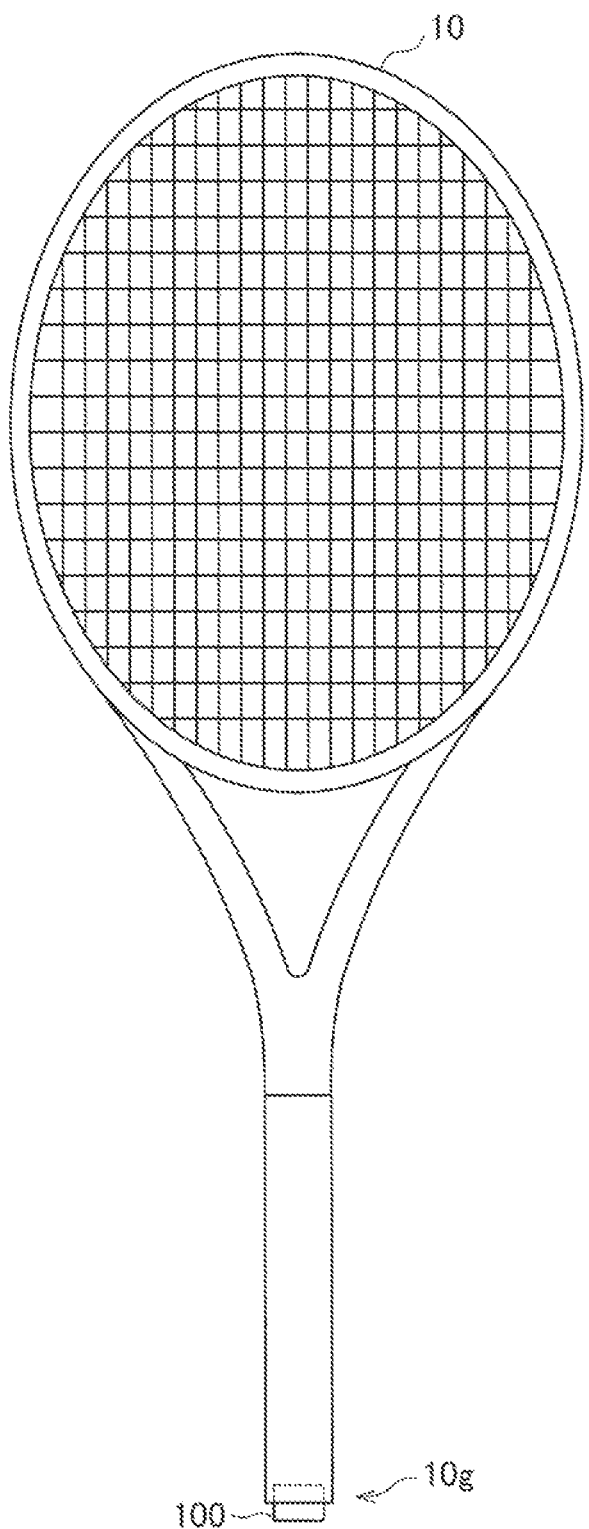
FIG. 1 is an explanatory diagram illustrating a position at which a sensor device is fitted on a hitting tool according to a first embodiment of the present disclosure.
Figure 2:
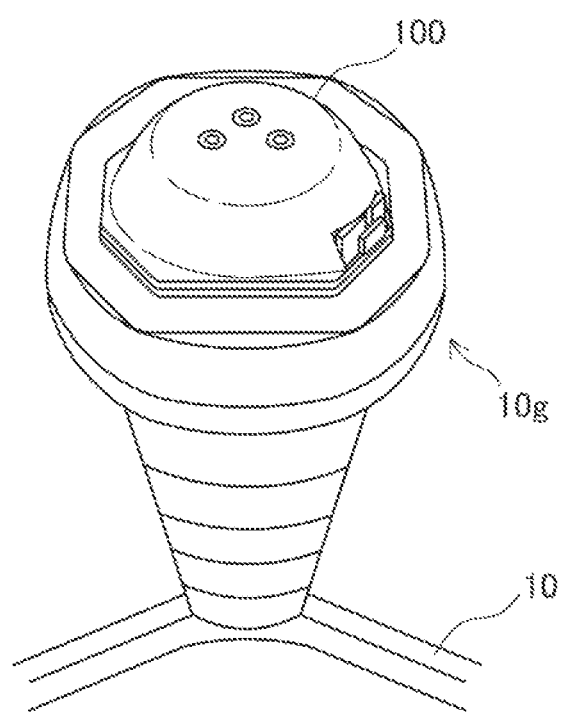
FIG. 2 is an explanatory diagram illustrating a position at which a sensor device is fitted on a hitting tool according to the first embodiment of the present disclosure.

FIGS. 1 and 2 are explanatory diagrams illustrating a position at which a sensor device is fitted on a hitting tool according to a first embodiment of the present disclosure. Referring to FIG. 1, a sensor device 100 is fitted on a grip end 10g of a racket 10 in the embodiment. The grip end 10g has a cylindrical shape and a part of the sensor device 100 fits into the grip end 10g. As illustrated in FIG. 2, since the grip end 10g has a substantially octagonal cross-sectional shape, the sensor device 100 fitting into the grip end 10g also has a substantially octagonal cross-sectional shape.

In the embodiment, the racket 10 on which the sensor device 100 is fitted is a hitting tool that is used in tennis. An example of the hitting tool according to an embodiment of the present disclosure is not limited to a tennis racket. An embodiment of the present disclosure can be applied to hitting tools used in, for example, all sports such as a badminton racket, a table tennis paddle, a golf club, and a baseball bat.

Figure 3:
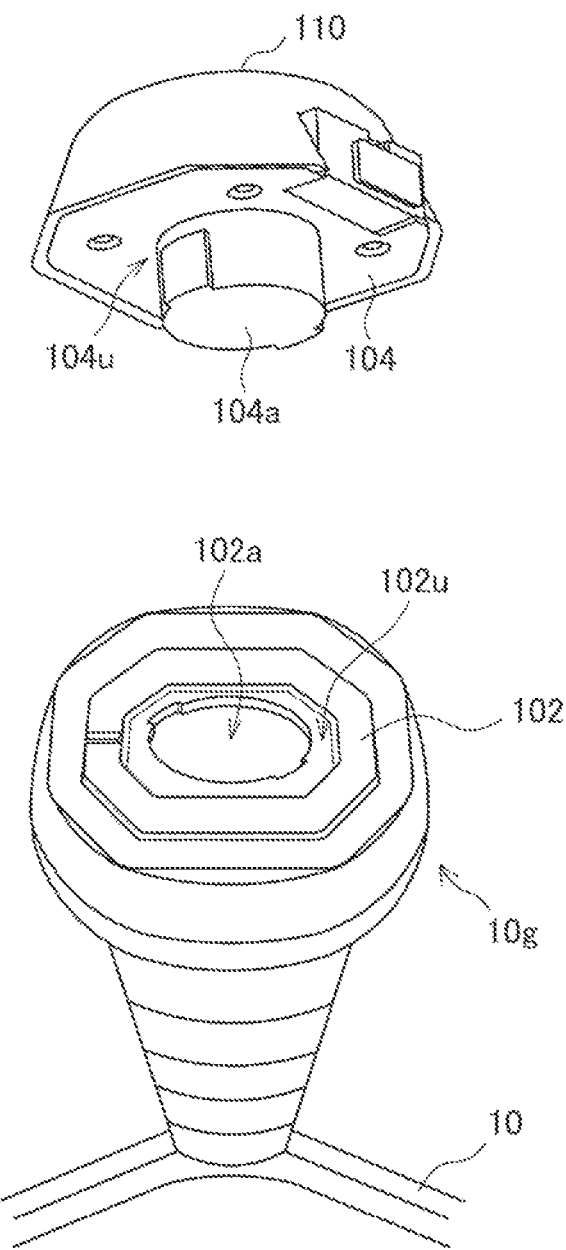
FIG. 3 is an explanatory diagram illustrating a schematic configuration of the sensor device according to the first embodiment of the present disclosure.

FIG. 3 is an explanatory diagram illustrating a schematic configuration of the sensor device according to the first embodiment of the present disclosure. Referring to FIG. 3, the sensor device 100 includes a fitting member 102, a base member 104, and an exterior member 110. In the example illustrated in the drawing, the base member 104 is detachably mounted on the fitting member 102 and the fitting member 102 fits into the grip end 10g of the racket 10 so that the base member 104 is fitted on the racket 10. The exterior member 110 covers a sensor, a communication device, and the like disposed on the base member 104 to protect them. The fitting member 102 is a member that is independent from the grip end 10g to form a fitting structure for fitting the base member 104 on the grip end 10g.

More specifically, the fitting member 102 has an octagonal pillar portion fitting into the grip end 10g, and an opening 102g leading to the inside of the octagonal pillar portion is formed on an upper surface 102u of the fitting member 102 facing the base member 104. A cylindrical protrusion 104a corresponding to the opening 102a is formed on a lower surface 104u of the base member 104. The protrusion 104a is inserted into the opening 102a so that the base member 104 is mounted on the fitting member 102. In the embodiment, when a partial overhang in a circumferential direction provided in the protrusion 104a is adjusted with a notch of the opening 102a, the protrusion 104a is inserted into the opening 102a. Thereafter, by rotating the base member 104 with respect to the fitting member 102, the base member 104 is fixed to the fitting member 102.

Figure 4:
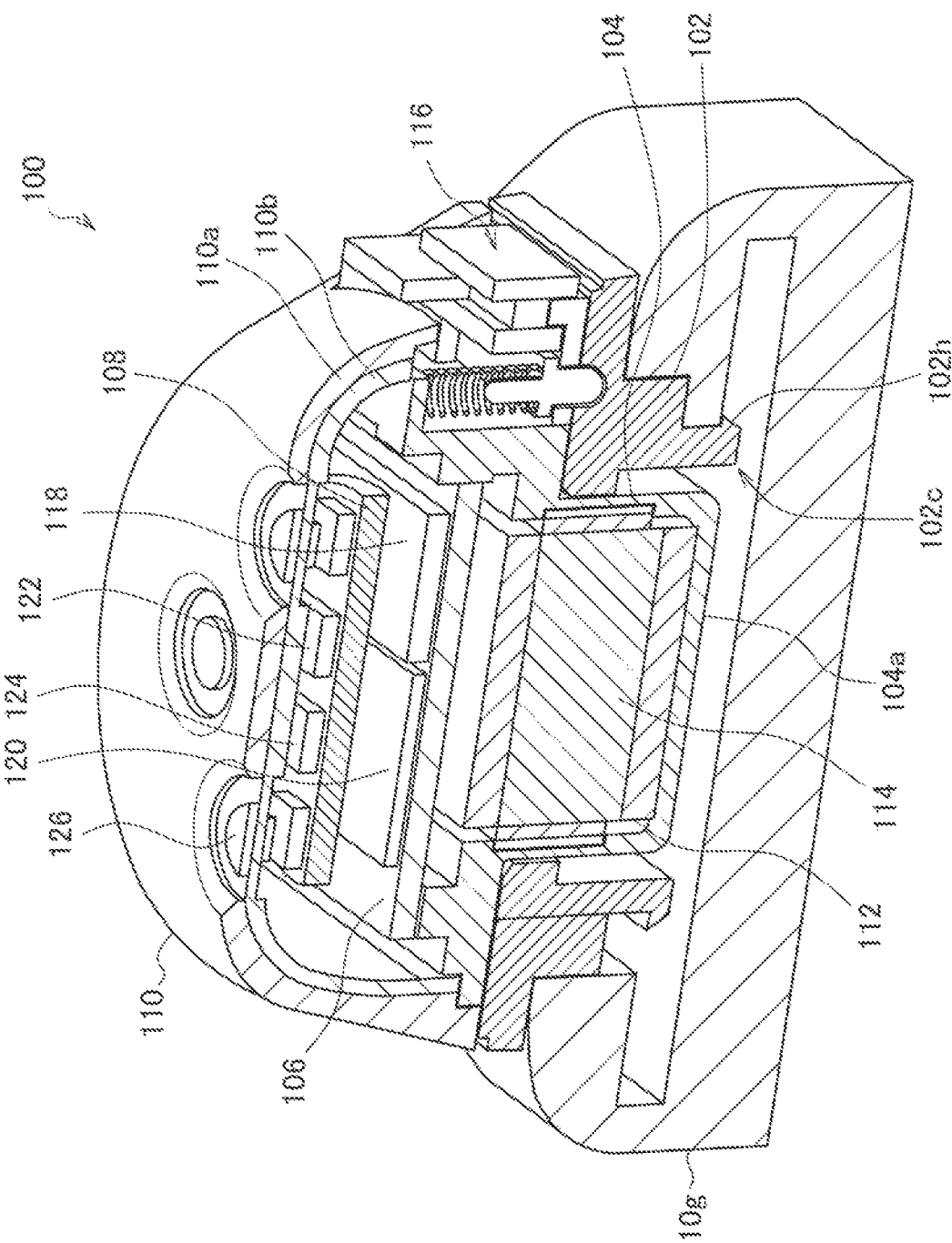
FIG. 4 is a cutaway perspective view illustrating the sensor device according to the first embodiment of the present disclosure.
Figure 5:
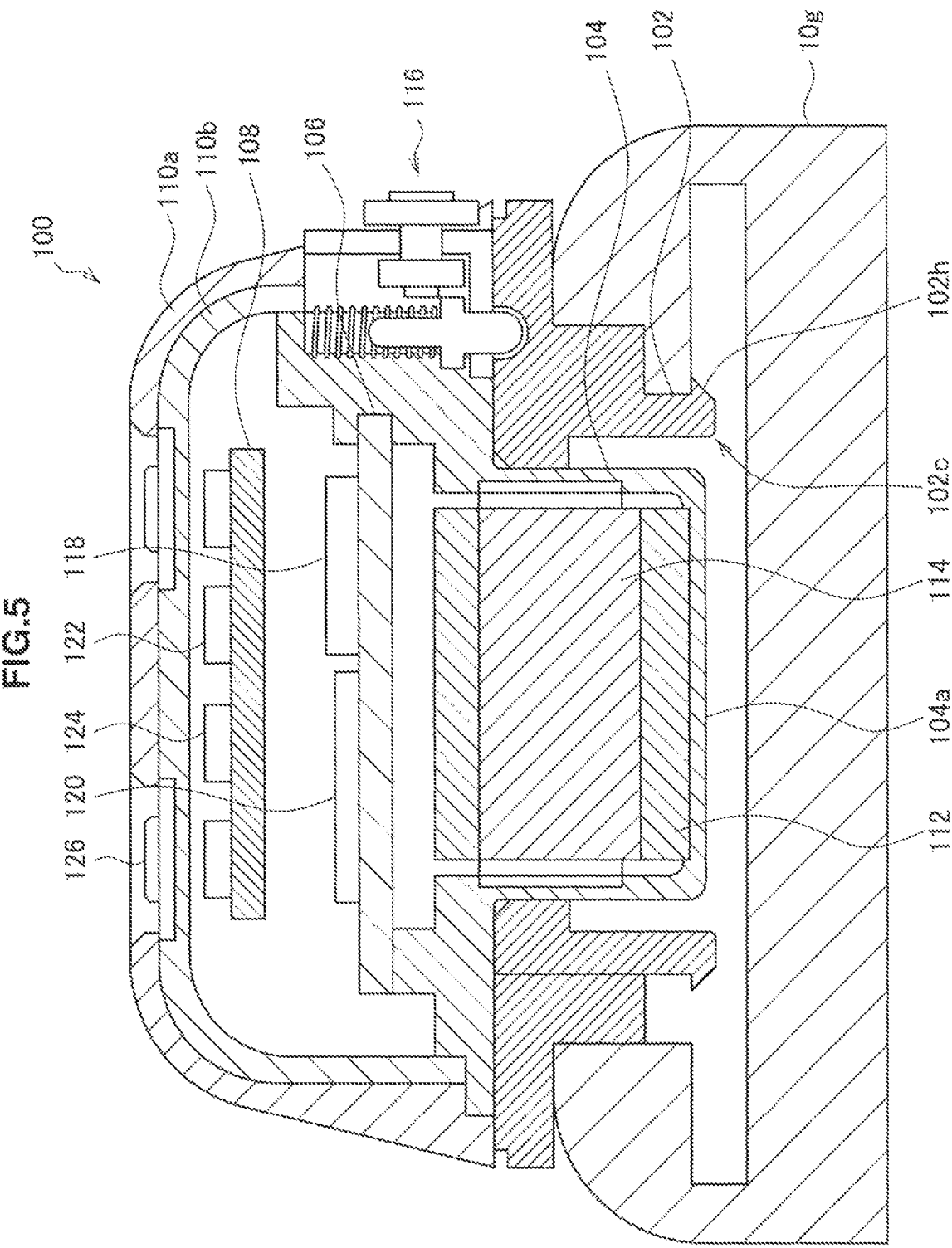
FIG. 5 is a sectional view illustrating the sensor device illustrated in FIG. 4.

FIG. 4 is a cutaway perspective view illustrating the sensor device according to the first embodiment of the present disclosure. FIG. 5 is a sectional view illustrating the sensor device illustrated in FIG. 4. The cross-sectional surface of FIG. 5 is identical to the cutaway surface of FIG. 4. Hereinafter, the configuration of the sensor device 100 according to the embodiment will be described in detail with reference to the drawings.

The fitting member 102 has a shape corresponding to the shape of the fitting portion of the racket 10. In the embodiment, as such a shape, the fitting member 102 has an octagonal pillar portion 102c fitting into the grip end 10g of the racket 10. In the example illustrated in the drawing, the octagonal pillar portion 102c has a shape corresponding to the inner wall surface of the grip end 10g, and thus the fitting member 102 can be brought into close contact with the grip end 10g. A latch claw 102h may be provided at a tip end of the octagonal pillar portion 102c.

In such a shape, the fitting member 102 fits into the grip end 10g to be fixed, and thus a motion of acceleration, angular velocity, vibration or the like occurring in the racket 10 is delivered from the grip end 10g. The fitting member 102 supports the base member 104 mounted thereon and delivers a motion of the racket 10 delivered from the grip end 10g via the octagonal pillar portion 102c to the base member 104.

The base member 104 is detachably mounted on the fitting member 102 to form a base of another member of the sensor device 100. A sensor substrate 106 is joined to the base member 104, and a communication substrate 108 and an exterior member 110 are directly or indirectly supported by the base member 104. As will be described below, the base member 104 comes into contact with the fitting member 102 by line contact or point contact so that a motion of acceleration, angular velocity, vibration or the like delivered from the grip end 10g is delivered from the fitting member 102.

In the embodiment, a battery case 112 is internally included inside the cylindrical protrusion 104a of the base member 104 penetrating into the octagonal pillar portion 102c of the fitting member 102. A battery 114 is accommodated in the battery case 112. Thus, an accommodation portion for the battery 114 is disposed inside the grip end 10g so that a portion of the sensor device 100 bulging outside the grip end 10g can be further decreased, and the battery 14 is distant from a communication circuit 122 to be described below so that it is possible to reduce an influence on communication of the communication circuit 122.

Here, the base member 104 may be detachably mounted on the fitting member 102. For example, as illustrated in FIG. 6, there are various variations of the shape of the grip end 10g of the racket 10. However, since the base member 104 and the fitting member 102 can be detachably mounted, the base member 104 and another member (hereinafter referred to as a body portion along with the base member 104) disposed on the base member 104 can be standardized by matching the shape of the fitting member 102 to each grip end 10g.

In such a configuration, for example, since many members can be standardized in the manufacturing of the sensor device 100, productivity can be improved. When the user owns a plurality of rackets 10, the fitting member 102 with a shape corresponding to the grip end 10g of each racket 10 can be prepared and the common body portion can be used instead. When the common body portion can be used, economy can be realized from the viewpoint of the user and the same sensor can be used when playing with another racket. Therefore, there is also an advantage from the viewpoint of continuously acquiring sensor data.

When the base member 104 is detachably mounted on the fitting member 102, for example, a lock mechanism 116 may be provided in the base member 104 to prevent the base member 104 from coming off of the fitting member 102 and prevent the body portion from falling down during play. The configuration of the lock mechanism 116 will be described below.

FIG. 6 is a diagram illustrating several examples of the grip end 10g. For example, as illustrated in FIGS. 6A and 6B, the grip end 10g can have an internal octagonal shape. However, as apparent with reference to FIGS. 6A and 6B, the sizes of the internal octagonal portions can differ depending on rackets. For example, as illustrated in FIG. 6C, the grip end 10g has an internal elliptical shape in some cases. Thus, an embodiment of the present disclosure is not limited to the grip end of the racket and the shape of each portion of a hitting tool differs according to, for example, a maker. Therefore, it is important that the sensor device can be easily fitted on hitting tools with different shapes and not easily come out even when the hitting tool is swung or a ball is hit with the hitting tool.

Referring back to FIGS. 4 and 5, the sensor substrate 106 is joined to the base member 104. For example, a sensor 118 and a preprocessing circuit 120 amplifying data detected by the sensor 118 or filtering data equal to or less than a threshold value can be disposed on the sensor substrate 106. Examples of the sensor 118 can include an acceleration sensor, a gyro sensor, and a geomagnetic sensor. Examples of the acceleration sensor may include a uniaxial shock sensor detecting an impact occurring in the racket 10 and a triaxial motion sensor detecting acceleration of the racket 10 at a higher resolution than the shock sensor.

Here, since the sensor substrate 106 is joined to the base member 104, a motion such as vibration, acceleration, or angular velocity occurring in the racket 10 is delivered from the grip end 10g via the fitting member 102 and the base member 104. The sensor 118 detects the motion such as vibration, acceleration, or angular velocity delivered up to the sensor substrate 106 in this way as a motion of the racket 10. Accordingly, the motion such as vibration, acceleration, or angular velocity occurring in the racket 10 is preferably delivered to the sensor 118 while the characteristics of the motion are maintained as much as possible.

Accordingly, in the embodiment, by realizing rigid connection between the grip end 10g and the fitting member 102, between the fitting member 102 and the base member 104, and between the base member 104 and the sensor substrate 106 without providing a buffer member such as an elastomer, a motion of the racket 10 is delivered to the sensor 118 as precisely as possible.

The members along a delivery route of the motion of the racket 10, that is, the fitting member 102, the base member 104, and the sensor substrate 106, preferably have materials and shapes for preserving frequency characteristics of vibration which is one of the motions occurring in the racket 10. For the shapes, for example, cross-sectional areas may be ensured to some extent in each member and an embodiment of the present disclosure is not limited to the shapes illustrated in the examples. For the materials, for example, in the case of the tennis racket 10, a swing feature is shown in vibration of a range equal to or less than about 2 kHz. Therefore, for example, a polycarbonate or a hard metal is preferably used for each member so that the frequency characteristics of this range can be preserved.

In the case of the tennis racket 10, a silicon-based material is not preferable since the frequency characteristics are not preserved. As another example, in the case of a golf club, a switching feature is shown in vibration of a range equal to or less than about 10 kHz. Therefore, a material of each member is preferably selected so that the frequency characteristics of this range can be preserved.

Figure 7:
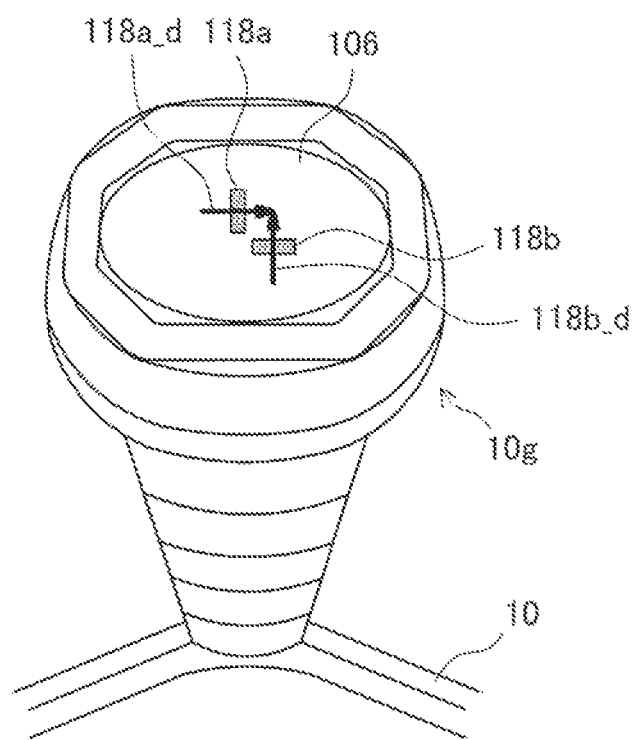
FIG. 7 is a diagram illustrating a first example of sensor disposition in the sensor device according to the first embodiment of the present disclosure.
Figure 8:
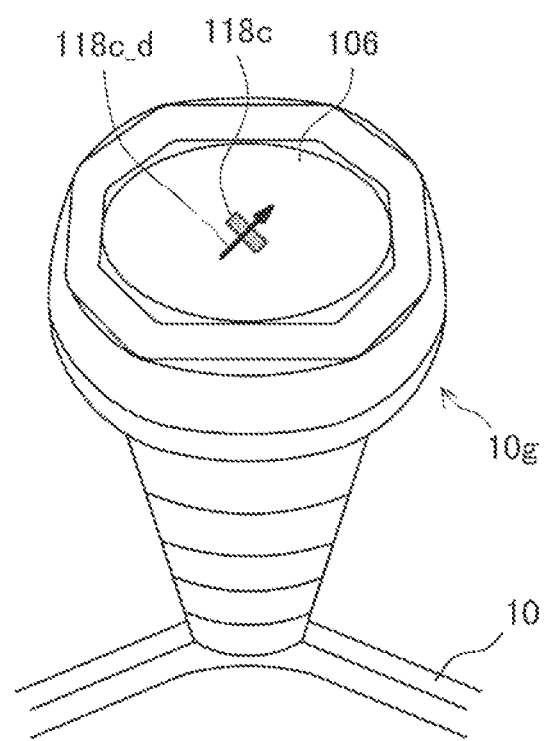
FIG. 8 is a diagram illustrating a second example of sensor disposition in the sensor device according to the first embodiment of the present disclosure.

Here, examples of detection direction disposition of the sensor 118 are illustrated in FIGS. 7 and 8. FIG. 7 is a diagram illustrating a first example of sensor disposition in the sensor device according to the first embodiment of the present disclosure. FIG. 8 is a diagram illustrating a second example of the sensor device in the sensor device according to the first embodiment of the present disclosure.

In the first example illustrated in FIG. 7, two sensors 118a and 118b are disposed on the sensor substrate 106 so that detection directions 118a_d and 118b_d are orthogonal to each other. The shape of the sensor substrate 106 is schematically illustrated to show a relation between the racket 10 and each detection direction and is not necessarily identical to the shape of the sensor substrate illustrated in other drawings.

In the example illustrated in the drawing, the detection direction 118a_d is a direction parallel to a hitting plane of the racket 10 and the detection direction 118b_d is perpendicular to the hitting plane of the racket 10. In such disposition, for example, it is possible to extract the frequency characteristics of the vibration occurring in the racket 10 from a detection result of the sensor 118b and extract a distribution of the vibration on the hitting plane of the racket 10 from a detection result of the sensor 118a.

Even when the detection directions are not parallel or perpendicular to the hitting plane, the same information can be extracted by separating detected vibration into two detection directions in a direction parallel to the hitting plane and a direction perpendicular to the hitting plane. However, the two detection directions are preferably orthogonal to each other in consideration of precision of the detection results after the separation. As in the example illustrated in the drawing, the precision of the detection result is the highest when the detection directions are identical to the direction parallel to the hitting plane and the direction perpendicular to the hitting plane.

In the second example illustrated in FIG. 8, a single sensor 118c is disposed on the sensor substrate 106 so that a detection direction 118c_d is oblique to the hitting plane of the racket 10. Even in this drawing, the shape of the sensor substrate 106 is schematically illustrated to show a relation between the racket 10 and the detection direction and is not necessarily identical to the shape of an actual sensor substrate.

In the example illustrated in the drawing, by separating the detection result of the single sensor 118c into a direction parallel to the hitting plane and a direction perpendicular to the hitting plane, it is possible to extract information regarding the vibration frequency characteristics of the vibration occurring in the direction perpendicular to the hitting plane and information regarding a distribution of the vibration on the hitting plane shown by the vibration in the direction parallel to the hitting plane.

In the foregoing method, two sensors are necessary. However, a method realized by one sensor at lower cost can also be considered, as illustrated in FIG. 8. As illustrated in the drawing, the detection direction may be inclined at about 45 degrees with respect to the hitting plane. Alternatively, the sensor 118c may be disposed at an asymmetric position deviated from the central axis of the hitting plane of the racket 10 and a distribution of vibration on the hitting plane may be considered to be symmetric to the central axis. The precision of the detection result is higher when a plurality of sensors are disposed as in the foregoing first example.

Referring back to FIGS. 4 and 5, the communication substrate 108 is indirectly connected to the base member 104. A communication circuit 122, an antenna 124, and the like transmitting the detection result of a motion of the racket 10 detected by the sensor 118 and processed by the preprocessing circuit 120 to an external device, more specifically, an analysis device, can be disposed on the communication substrate 108. For example, wireless communication is used to transmit the detection result. A communication scheme is not particularly limited. For example, when the analysis device of a transmission destination is near the sensor device 100, short-range wireless communication such as Bluetooth (registered trademark) or a wireless local area network (LAN) can be used. As in the example illustrated in the drawing, by disposing the communication circuit 122 and the antenna 124 on an opposite side to the battery case 112 with the base member 104 and the sensor substrate 106 interposed therebetween, it is possible to minimize an influence on communication due to, for example, blocking of radio waves by a metal included in the battery case 112 or the battery 114.

Further, a control circuit (not illustrated) controlling an operation of the communication circuit 122 may be provided on the communication substrate 108. The control circuit controls execution or pause of the transmission of the detection result, for example, according to a user manipulation acquired via a button 126 or the like that is provided, as necessary. Similarly, a control circuit (not illustrated) controlling an operation of the preprocessing circuit 120 (capable of controlling an operation of the sensor 118 when the sensor 118 includes an active type sensor) may be provided on the sensor substrate 106. Alternatively, a control circuit controlling both of the communication circuit 122 and the preprocessing circuit 120 may be provided on the sensor substrate 106 or the communication substrate 108.

Here, unlike the sensor substrate 106, a motion such as vibration, acceleration, or angular velocity occurring in the racket 10 may not be delivered to the communication substrate 108. That is, vibration, acceleration, angular velocity, or the like may be attenuated or denatured between the base member 104 and the communication substrate 108. Therefore, for example, the communication substrate 108 may be indirectly connected to the base member 104 or may be connected to the side of the exterior member 110 via a buffer member such as an elastomer in order to protect the communication circuit 122 or the like against vibration. Alternatively, when it is not particularly necessary to protect the communication circuit 122 or the like, the communication substrate 108 may be joined to the base member 104 as in the sensor substrate 106 so that vibration occurring in the racket 10 is delivered.

The exterior member 110 is provided on the base member 104 to cover the sensor substrate 106 and the communication substrate 108. The exterior member 110 can have a structure that protects the sensor 118 on the sensor substrate 106 and the communication circuit 122 on the communication substrate 108 from an external impact. An external impact occurs, for example, when the sensor device 100 fitted on the grip end 10g of the racket 10 collides with the body of a user, another mechanism such as a ball, or the ground.

For example, the exterior member 110 has a two-layered structure of the external soft portion 110a and an internal hard portion 110b, and the soft portion 110a may absorb an external impact to prevent the external impact from being delivered to the sensor 118, the communication circuit 122, or the like. In this case, for example, the soft portion 110a can be formed of a material such as an elastomer and the hard portion 110b can be formed of a material such as acrylonitrile butadiene styrene (ABS) or a polycarbonate.

In the exterior member 110, a space may be formed between the sensor 118 and the communication circuit 122 to protect these members against an external impact. In the example illustrated in the drawing, a space is formed between the communication circuit 122 disposed on the communication substrate 108 and the exterior member 110 and a space is further formed between the sensor 118 disposed on the substrate 106 and the communication substrate 108 on the sensor 118, so that the foregoing structure is realized.

Figure 9:
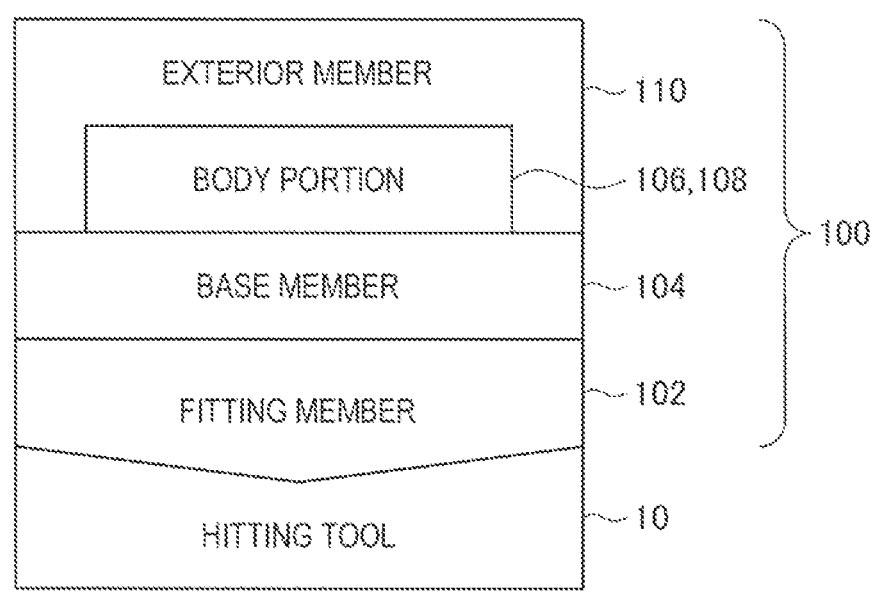
FIG. 9 is a diagram schematically illustrating the configuration of the sensor device according to the first embodiment of the present disclosure.

FIG. 9 is a diagram schematically illustrating the configuration of the sensor device according to the first embodiment of the present disclosure described above. In FIG. 9, the sensor device 100 is classified into the fitting member 102, the base member 104, the body portions 106 and 108, and the exterior member 110.

In the sensor device 100, as described above, the body portions 106 and 108 including the sensor or the communication unit are connected to the racket 10 via the base member 104 and the fitting member 102. Here, both of the fitting member 102 and the base member 104 have a material and a structure delivering a motion of the racket 10, so that a motion such as vibration, acceleration, or angular velocity occurring in the racket 10 is delivered to the sensors of the body portions 106 and 108 precisely.

When the delivery of vibration or the like from the racket 10 is allowed, the body portions 106 and 108 are covered with the exterior member 110, and thus the exterior member 110 protects the body portions 106 and 108 against an external impact, and unnecessary vibration or the like is prevented from being delivered to the sensor or the communication unit so that noise is prevented from being mixed in the detection result and the device is prevented from breaking due to an impact.

By detachably mounting the fitting member 102 on the base member 104, it is possible to cause the base member 104, the body portions 106 and 108, and the exterior member 110 to be standardized to correspond to various shapes which the fitting portion (the grip end 10g in the foregoing example) of the racket 10 can have by changing the fitting member 102.

(1-2. First Example of Junction Structure)

Figure 10:
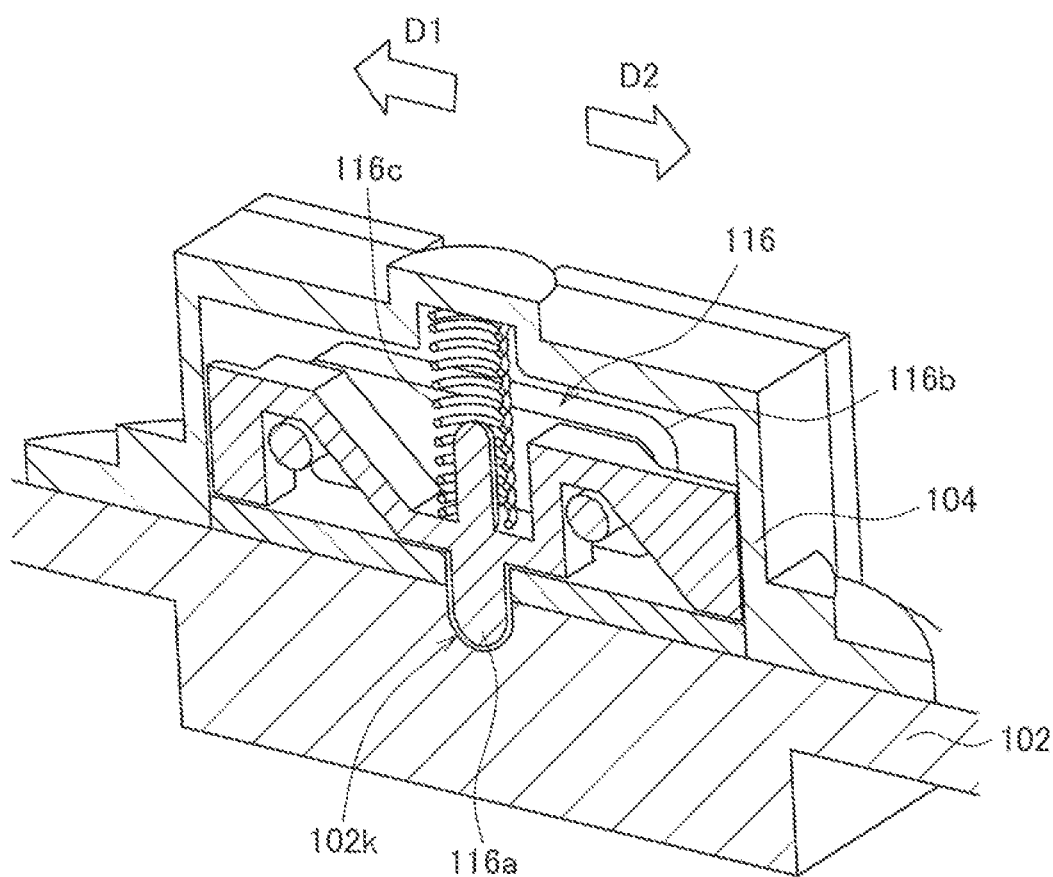
FIG. 10 is an explanatory diagram illustrating a lock mechanism in a first example of a junction structure between a fitting member and a base member of the sensor device according to the first embodiment of the present disclosure.

FIG. 10 is an explanatory diagram illustrating a lock mechanism in a first example of a junction structure between a fitting member and a base member of the sensor device according to the first embodiment of the present disclosure. Referring to FIG. 10, the lock mechanism 116 disposed on a surface on the base member 104 faces the fitting member 102 and includes a pin member 116a, a knob 116b, and a spring 116c.

In the embodiment, for example, as described with reference to FIG. 3, the base member 104 is fixed to the fitting member 102 by rotating the base member 104 with respect to the fitting member 102. Thus, by causing the pin member 116a that is pressed downward by the spring 116c to protrude from the base member 104 and the pin member 116a to penetrate into a hole portion 102k formed at a position corresponding to the fitting member 102 in the lock mechanism 116, rotation of the base member 104 in the fixed state to the fitting member 102 is prevented. Thus, for example, during play, the base member 104 is prevented from coming off of the fitting member 102 and the body portion is prevented from falling.

When the user intentionally takes the base member 104 off of the fitting member 102, the user slides the knob 116b in a direction D2. Then, the pin member 116a ascends against the spring 116c due to an engagement structure of the knob 116b and the pin member 116a and slips off of the hole portion 102k of the fitting member 102, as illustrated in the drawing. Accordingly, the user can detach the base member 104 from the fitting member 102 by rotating the base member 104 with respect to the fitting member 102.

In the lock mechanism 116 as in the example illustrated in the drawing, the direction D2 in which the knob 116b is slid to ascend the pin member 116a can be an opposite direction to a direction D1 in which the user turns the knob 16b to detach the base member 104 from the fitting member 102. Thus, for example, even when the user erroneously manipulates the knob 116b in the direction D2, the base member 104 is prevented from being rotated in the same direction and the base member 104 is prevented from coming off of the fitting member 102.

Figure 11:
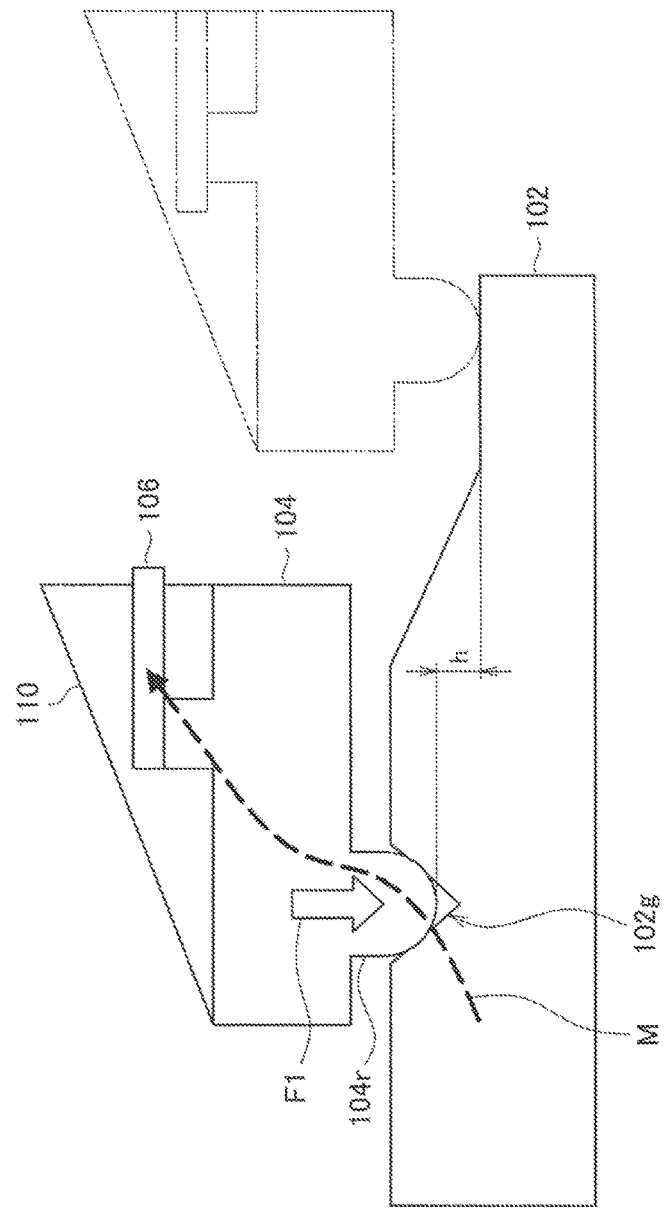
FIG. 11 is an explanatory diagram illustrating a first example of a line contact structure in the first example of the junction structure of the fitting member and the base member of the sensor device according to the first embodiment of the present disclosure.
Figure 12:
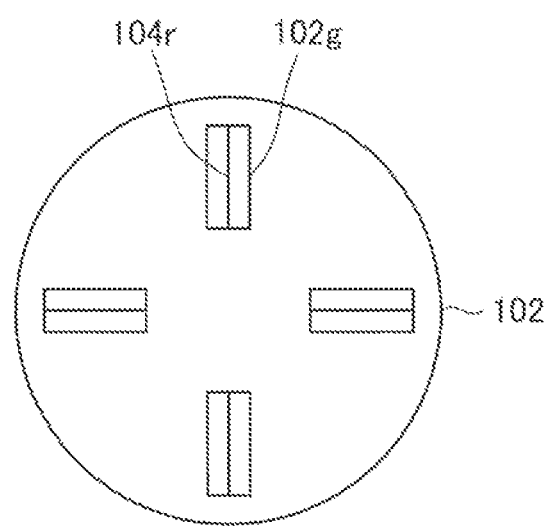
FIG. 12 is an explanatory diagram illustrating the first example of a line contact structure in the first example of the junction structure of the fitting member and the base member of the sensor device according to the first embodiment of the present disclosure.

FIGS. 11 and 12 are explanatory diagrams illustrating a first example of a line contact structure in the first example of the junction structure of the fitting member and the base member of the sensor device according to the first embodiment of the present disclosure. FIG. 11 is a schematic longitudinal sectional view illustrating a junction portion and FIG. 12 is a schematic cross-sectional view illustrating the junction portion. Since both of the drawings are schematic diagrams, the shape of each member is not necessarily identical to the shapes illustrated in other drawings. Referring to FIG. 11, a rib 104r protruding toward the facing fitting member 102 is formed on the lower surface of the base member 104. On the other hand, a groove 102g corresponding to the rib 104r is formed on the upper surface of the fitting member 102.

When the base member 104 is mounted on the fitting member 102, the rib 104r is thrust into the groove 102g by rotating the base member 104 with respect to the fitting member 102, as described above. Here, as illustrated in the drawings, the groove 102g is formed in a portion higher than the other portions of the upper surface of the fitting member 102. Therefore, the base member 104 is lifted by a height h more than the other portions to be elastically deformed in the portion in which the rib 104r is thrust into the groove 102g. The rib 104r is pressed in the groove 102g by a restoring force F1 from the elastic deformation.

In the first example, a connection structure by the rib 104r and the groove 102g is formed in a plurality of spots (for example, three or more spots) of the junction portion, as illustrated in FIG. 12. By joining the base member 104 and the fitting member 102 strongly by line contact or point contact in such portions, for example, there is less rattling than, for example, when these members are entirely joined by surface contact. A motion M of the racket 10 can be delivered from the fitting member 102 to the base member 104 by stable junction.

Figure 13:
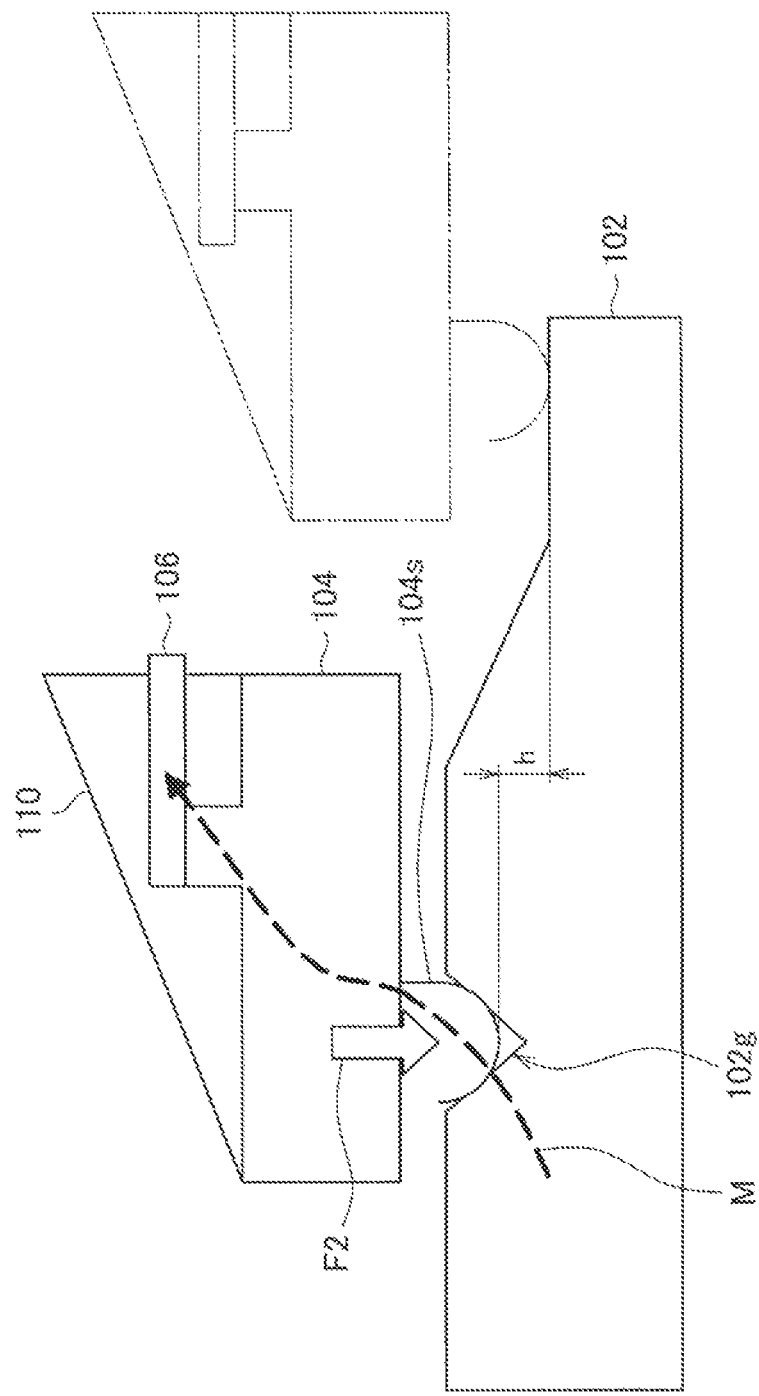
FIG. 13 is an explanatory diagram illustrating a second example of a line contact structure in the first example of the junction structure of the fitting member and the base member of the sensor device according to the first embodiment of the present disclosure.

FIG. 13 is an explanatory diagram illustrating a second example of the line contact structure in the first example of the junction structure of the fitting member and the base member of the sensor device according to the first embodiment of the present disclosure. FIG. 13 is a longitudinal sectional view illustrating the junction portion. Since FIG. 13 is a schematic diagram, the shape of each member is not necessarily identical to the shapes illustrated in the other diagrams. Referring to FIG. 13, a flat spring 104s protruding toward the facing fitting member 102 is disposed on the lower surface of the base member 104. On the other hand, a groove 102g corresponding to the flat spring 104s is formed on the upper surface of the fitting member 102.

When the base member 104 is mounted on the fitting member 102, the flat spring 104s is thrust into the groove 102g by rotating the base member 104 with respect to the fitting member 102, as described above. Here, as illustrated in the drawings, the groove 102g is formed in a portion higher than the other portions of the upper surface of the fitting member 102. Therefore, the flat spring 104s is lifted by a height h more than the other portions to be elastically deformed in the portion in which the flat spring 104s is thrust into the groove 102g. The flat spring 104s is pressed in the groove 102g by a restoring force F2 from the elastic deformation.

In the second example, a connection structure by the flat spring 104s and the groove 102g is formed in a plurality of spots (for example, three or more spots) of the junction portion, as in the first example illustrated in FIG. 12. By joining the base member 104 and the fitting member 102 strongly by line contact or point contact in such portions, for example, there is less rattling than when these members are entirely joined by surface contact. A motion M of the racket 10 can be delivered from the fitting member 102 to the base member 104 by stable junction.

As the advantage of the second example compared to the foregoing first example, when the sensor device 100 is used for a long time, the base member 104 is plastically deformed since the restoring force F1 generated by the elastic deformation of the base member 104 of which elasticity is not considerably high is used in the first example. Thus, the sufficient restoring force F1 is not obtainable and there is a possibility of the mounting on the fitting member 102 being difficult. On the other hand, in the second example, the possibility of the plastic deformation occurring is lower than in the first example since the restoring force F2 occurring due to the plastic deformation of the flat spring 104s with high elasticity is used.

(1-3. Second Example of Junction Structure)

Figure 14:
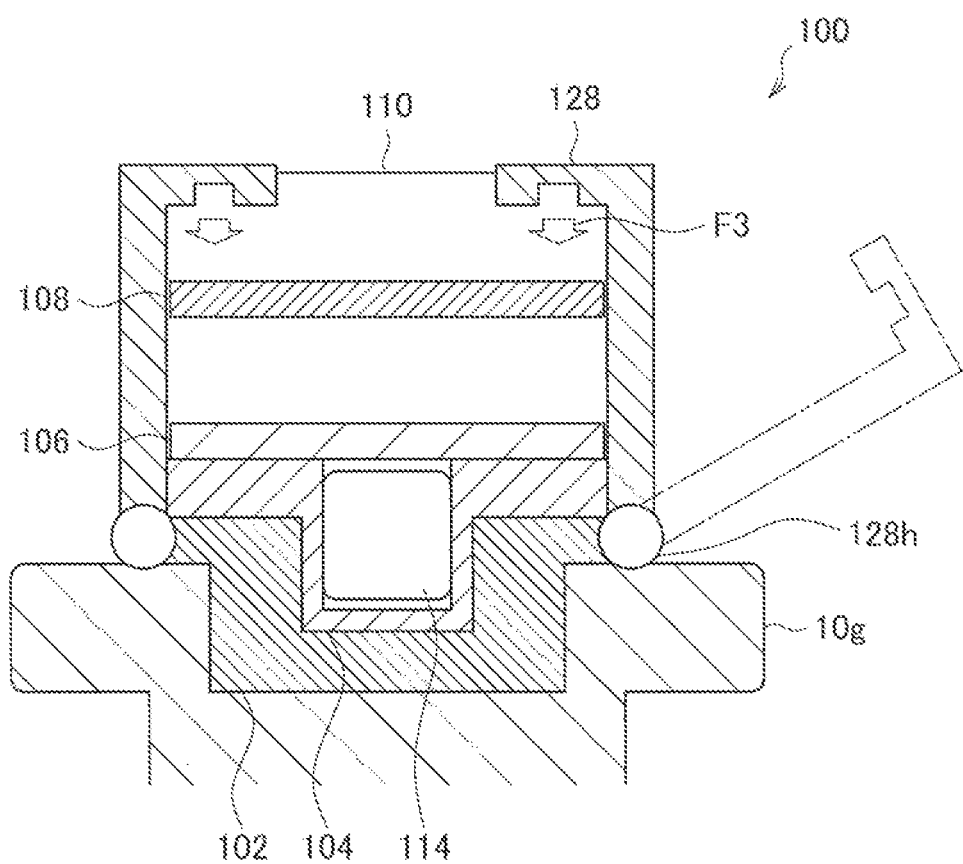
FIG. 14 is an explanatory diagram illustrating a second example of the junction structure between the fitting member and the base member of the sensor device according to the first embodiment of the present disclosure.
Figure 15:
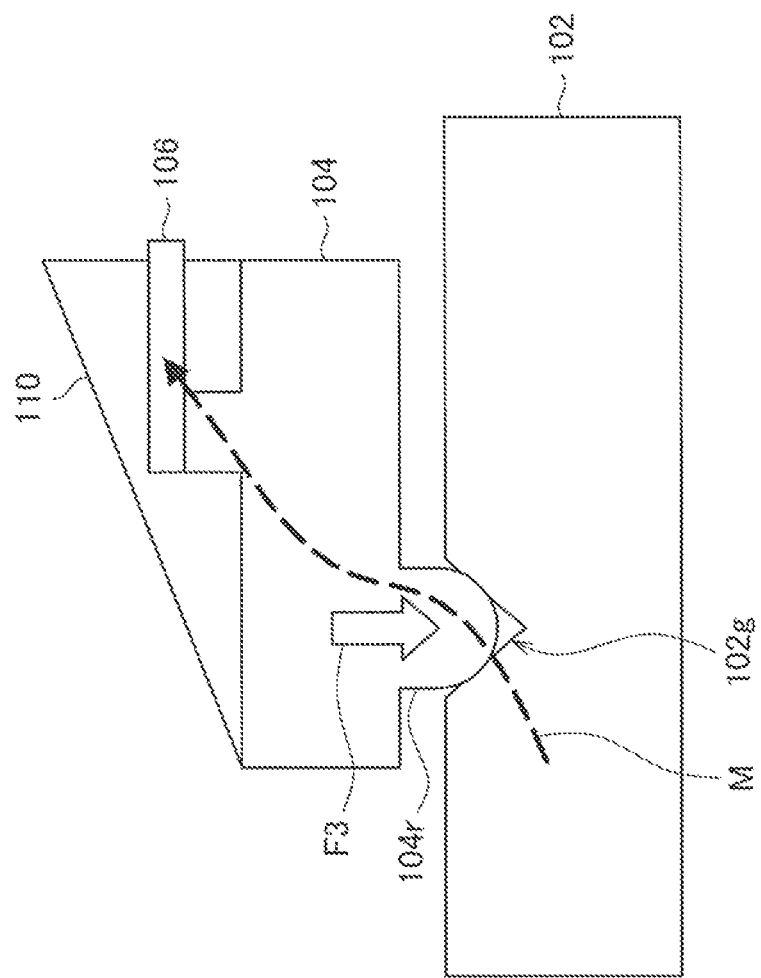
FIG. 15 is an explanatory diagram illustrating the second example of the junction structure between the fitting member and the base member of the sensor device according to the first embodiment of the present disclosure.

FIGS. 14 and 15 are explanatory diagrams illustrating a second example of the junction structure between the fitting member and the base member of the sensor device according to the first embodiment of the present disclosure. FIG. 14 is a longitudinal sectional view illustrating the entire sensor device. FIG. 15 is a schematic longitudinal sectional view illustrating the junction portion. Since both of the drawings are schematic diagrams, the shape of each member is not necessarily identical to the shapes illustrated in the other diagrams.

In the second example, referring to FIG. 14, the body portion of the sensor device 100 including the base member 104, the sensor substrate 106, the communication substrate 108, and the exterior member 110 is appressed to the fitting member 102 located therebelow by an arm 128. The arm 128 has a hook shape and is connected to the fitting member 102 by a hinge 128h. The arm 128 is rotated about the hinge 128h so that the tip end of the hook shape is engaged with the upper surface of the body portion. For example, the internal dimension of the arm 128 in the vertical direction is substantially the same as the height of the body portion excluding the height of the rib 104r to be described below. Thus, the arm 128 presses the body portion against the fitting member 102.

In the second example, referring to FIG. 15, the rib 104r is formed on the lower surface of the base member 104 and the groove 102g is formed on the upper surface of the fitting member 102, as in the foregoing first example. In the case of the second example, however, the height of the portion in which the groove 102g is formed is the same as the other portions of the upper surface of the fitting member 102. In the example, since the rib 104r is pressed downward in the groove 102g by a force F3 by which the arm 128 presses the body portion downward, it is not necessary to realize a configuration such as the stepped difference of the fitting member 102 for obtaining a restoring force of the base member 104 as in the foregoing first example.

When the length of the arm 128 is decided, the elastic deformation of the base member 104 due to the forming of the rib 104r may be considered. The flat spring 104s may be disposed instead of the rib 104r as in the foregoing first example so that there is an allowable error to some extent in the dimensions of the arm 128 and the body portion.

(1-4. Third Example of Junction Structure)

Figure 16:
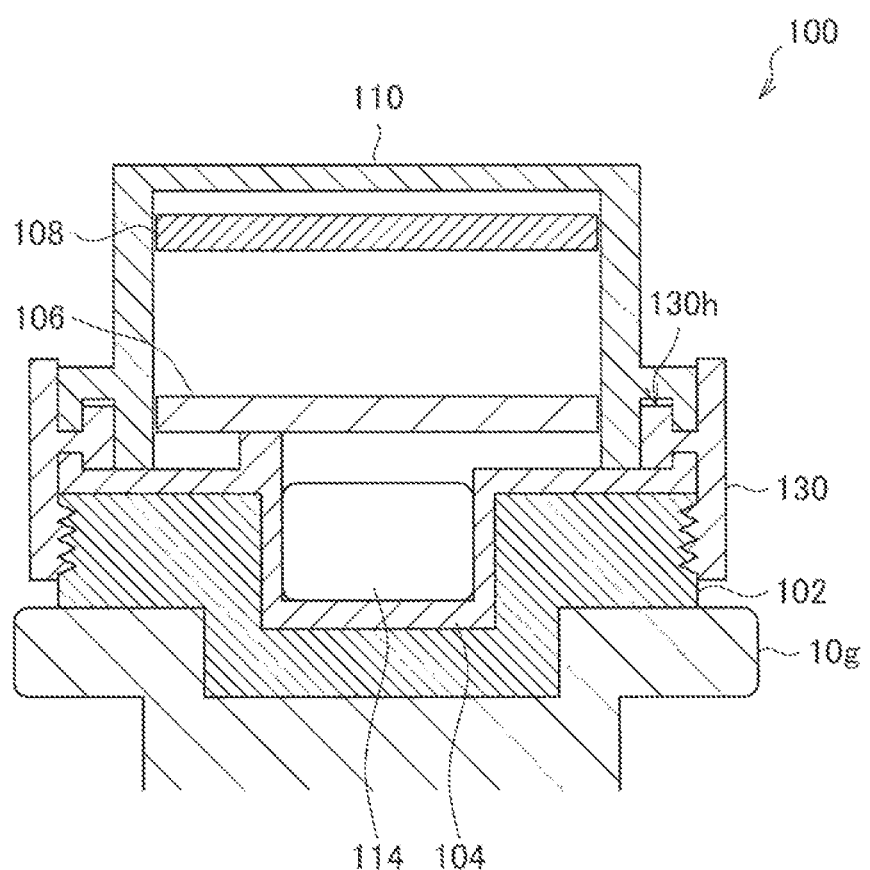
FIG. 16 is an explanatory diagram illustrating a third example of the junction structure between the fitting member and the base member of the sensor device according to the first embodiment of the present disclosure.

FIG. 16 is an explanatory diagram illustrating a third example of the junction structure between the fitting member and the base member of the sensor device according to the first embodiment of the present disclosure. FIG. 16 is a longitudinal sectional view illustrating the entire sensor device 100. Since FIG. 16 is a schematic diagram, the shape of each member is not necessarily identical to the shapes illustrated in the other diagrams. In the third example, referring to FIG. 16, the base member 104 is joined to the fitting member 102 by a screw-attached ring 130.

Screws are set on the inner circumferential surface of the screw-attached ring 130 and the outer circumferential surface of the fitting member 102, and the screws are engaged so that a force by which the screw-attached ring 130 presses the base member 104 against the fitting member 102 can be obtained. For example, as illustrated in the drawing, the screw-attached ring 130 includes an engagement portion 130h engaging with the upper surface of the base member 104, and the base member 104 is pressed against the fitting member 102 from the upper side by the engagement portion 130h. To prevent the screws from being loosened during play or the like, a lock such as a ratchet mechanism is preferably provided in the screw-attached ring 130.

Figure 17:
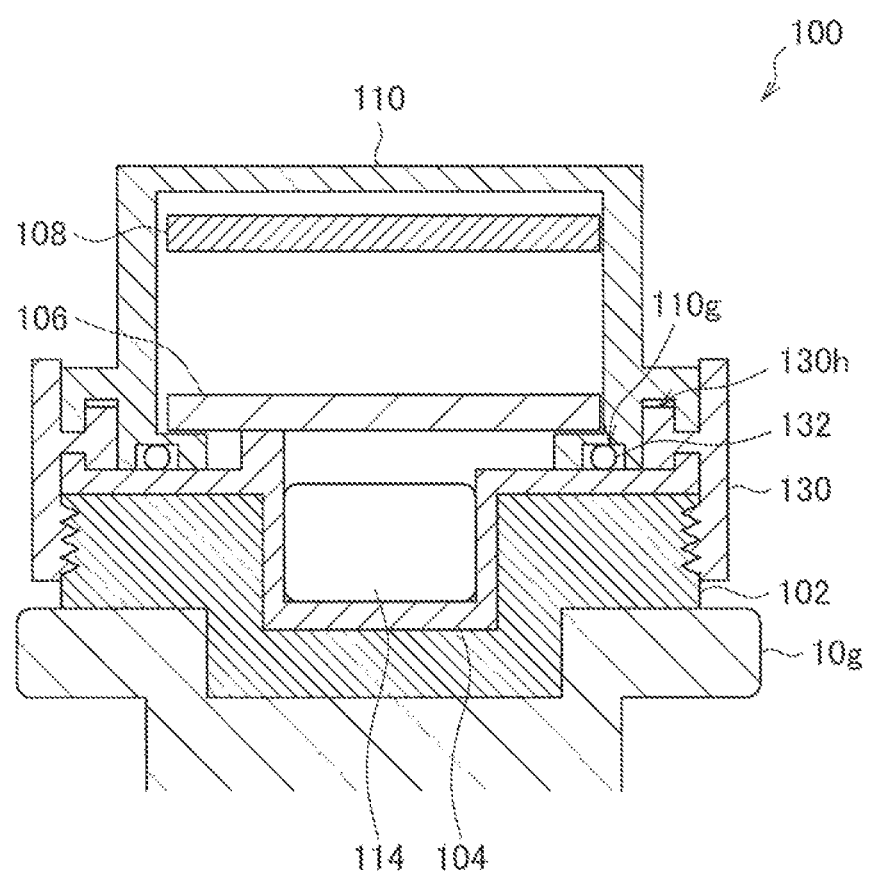
FIG. 17 is an explanatory diagram illustrating a modification of the third example of the junction structure between the fitting member and the base member of the sensor device according to the first embodiment of the present disclosure.

FIG. 17 is an explanatory diagram illustrating a modification of the third example of the junction structure between the fitting member and the base member of the sensor device according to the first embodiment of the present disclosure. Referring to FIG. 17, in the junction structure in which the screw-attached ring 130 is used as in FIG. 16, an O ring 132 is disposed in a groove 110g provided in a region in which the exterior member 110 comes into contact with the base member 104. By connecting the base member 104 to the exterior member 110 in such a waterproof structure, for example, circuit components provided in the sensor substrate 106 or the communication substrate 108 inside the exterior member 110 can be protected against from external water or moisture. The similar waterproof structure is not limited to the third example, but can also be applied to the foregoing first and second examples.

(1-5. Example of Charger Connection)

Figure 18:
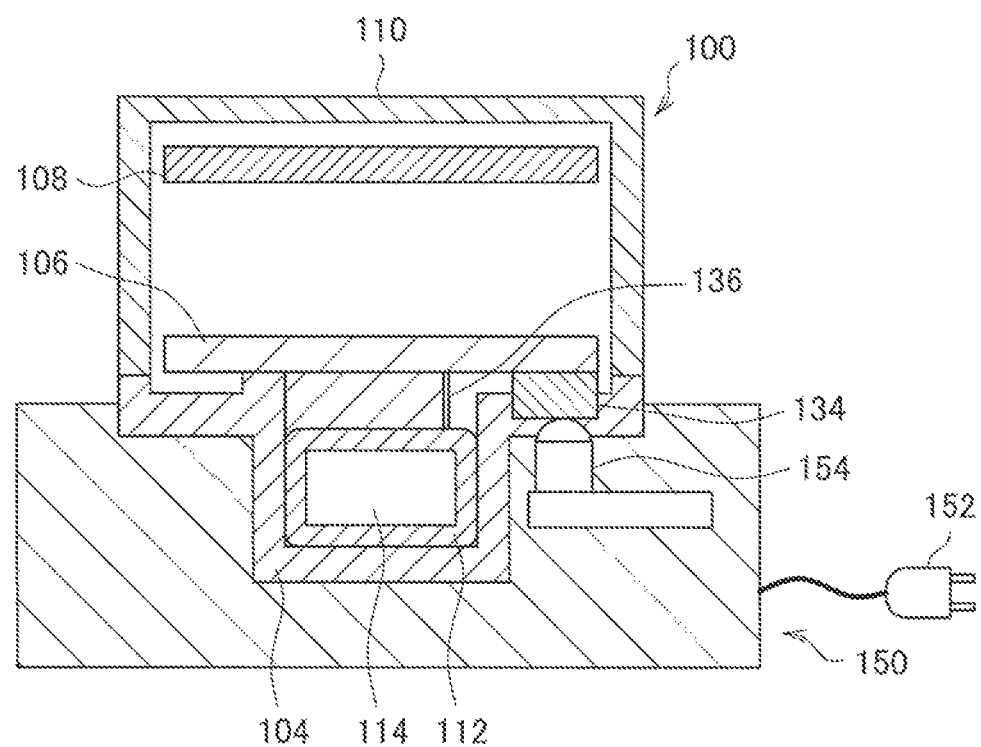
FIG. 18 is an explanatory diagram illustrating a connection example of a charger of the sensor device according to the first embodiment of the present disclosure.

FIG. 18 is an explanatory diagram illustrating a connection example of a charger of the sensor device according to the first embodiment of the present disclosure. FIG. 18 is a schematic longitudinal sectional view illustrating a state in which a part of the sensor device 100 is detached and connected to a charger 150. Since FIG. 18 is a schematic diagram, the shape of each member is not necessarily identical to the shapes illustrated in the other diagrams. Referring to FIG. 18, a part of the sensor device 100 including the base member 104 detached from the fitting member 102 is detachably mounted on the charger 150 that has a shape corresponding to a mounting portion of the base member 104 on the fitting member 102.

In this case, the sensor device 100 includes a connection terminal 134 that connects the battery 114 accommodated in the battery case 112 to a charging terminal 154 of the charger 150 when the base member 104 is mounted on the charger 150. When the charging terminal 154 slightly protrudes from a fitting surface on which the base member 104 is fitted on the charger 150 and comes into contact with the lower surface of the base member 104, a spring can also be provided together so that the base member 104 is pushed downward. On the other hand, on the lower surface of the base member 104, the connection terminal 134 is provided at a position at which the connection terminal 134 comes into contact with the charging terminal 154 when the base member 104 is mounted on the charger 150 to be fixed.

For example, the part of the sensor device 100 including the base member 104 is fixed to the charger 150 by inserting the protrusion 104a into the charger 150 and then rotating the base member 104 with respect to the charger 150, as in the case of the mounting on the fitting member 102, as described with reference to FIG. 3. When each terminal is disposed so that the connection terminal 134 comes into contact with the charging terminal 154 at the time of fixing to the charger 150, the part of the sensor device 100 is fixed to the charger 150 and the battery 114 is connected to an external power source via a connection wiring 136, the connection terminal 134, the charging terminal 154, and a power plug 152, so that charging starts. The user can connect the sensor device 100 to the charger 150 through the same operation as when the base member 104 is mounted on the fitting member 102.

2. Second Embodiment

Next, a second embodiment of the present disclosure will be described with reference to FIGS. 19 to 22. A sensor device according to the embodiment is fitted on a tennis racket as in the sensor device 100 according to the first embodiment. However, the sensor device is different from the sensor device 100 in that a fitting position is not a grip end but a tip end of a grip. Since other details are the same as those of the sensor device 100, the repeated description will be omitted below.

Figure 19:
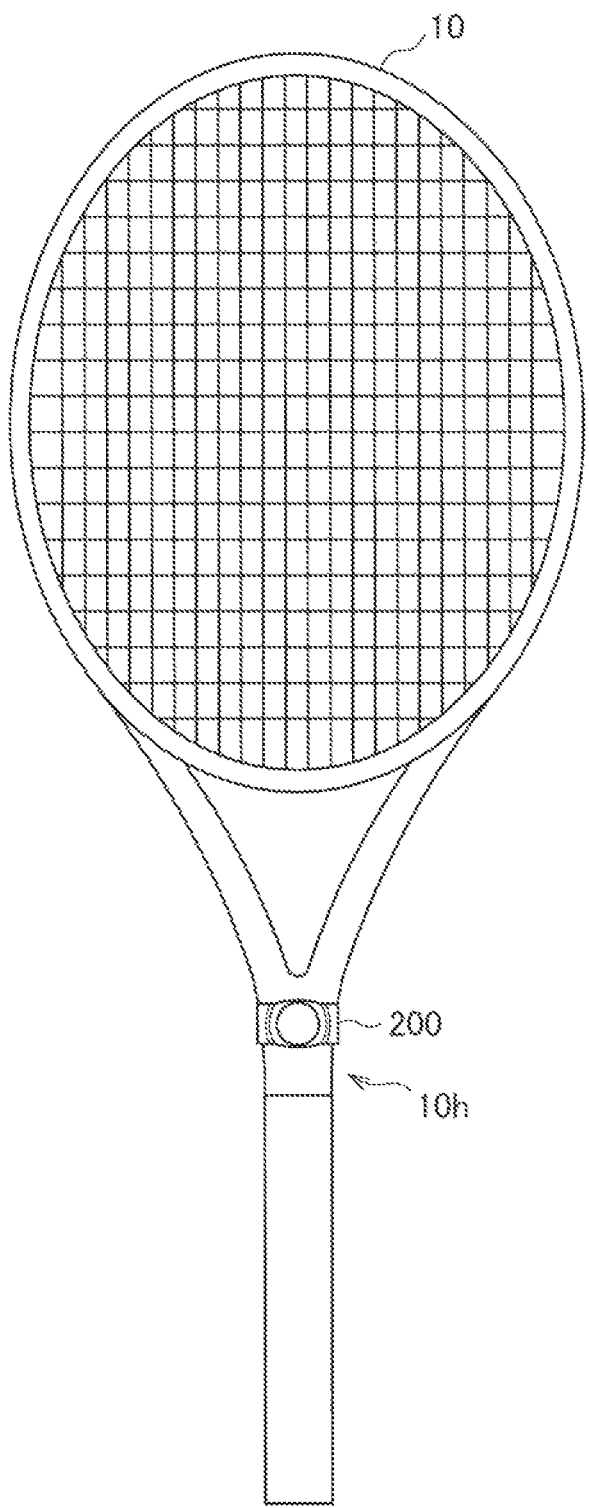
FIG. 19 is an explanatory diagram illustrating a position at which a sensor device is fitted on a hitting tool according to a second embodiment of the present disclosure.

FIG. 19 is an explanatory diagram illustrating a position at which a sensor device is fitted on a hitting tool according to the second embodiment of the present disclosure. In the embodiment, referring to FIG. 19, a sensor device 200 is fitted on a tip end of a grip 10h of a racket 10. The sensor device 200 is wound around the grip 10h to be fixed.

Figure 20:
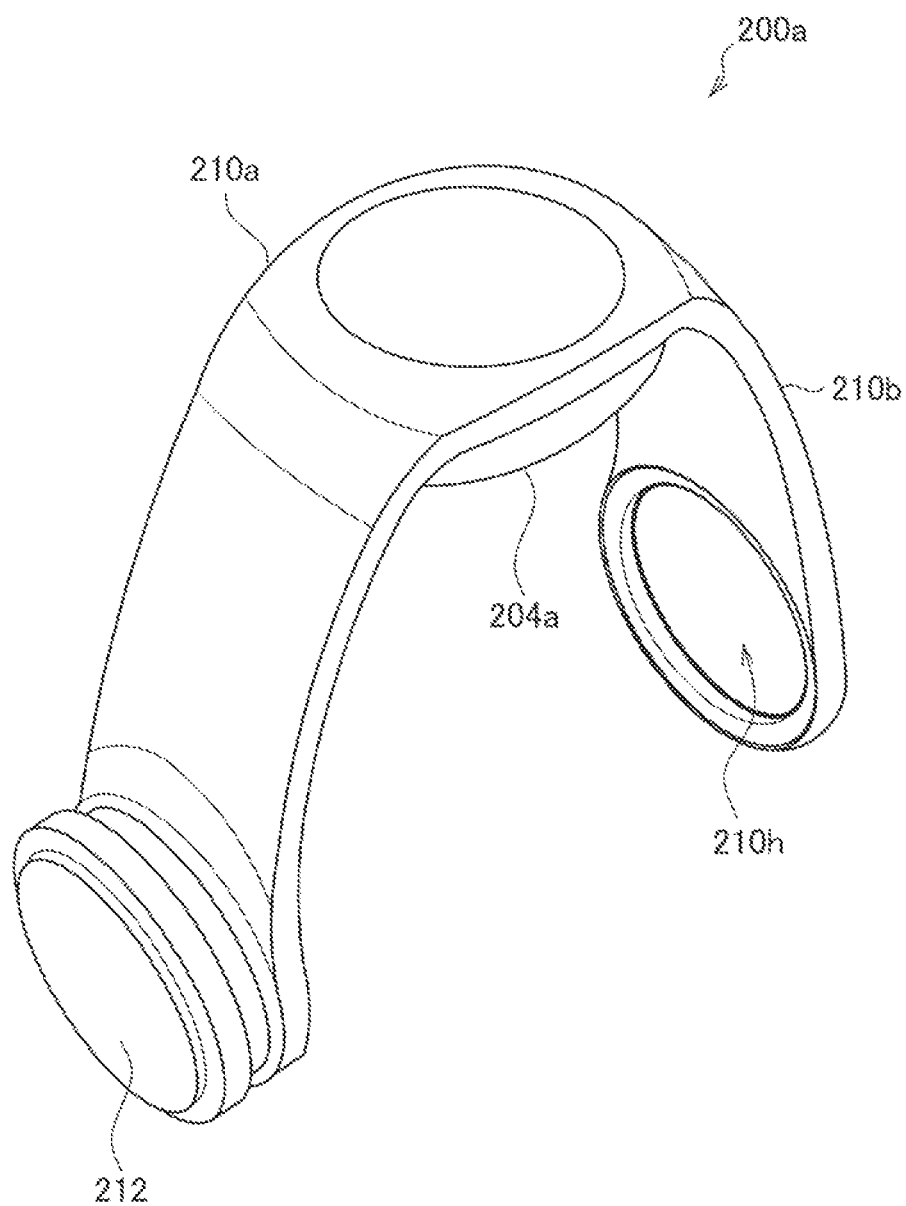
FIG. 20 is a schematic perspective view illustrating a first example of the sensor device according to the second embodiment of the present disclosure.

FIG. 20 is a schematic perspective view illustrating a first example of the sensor device according to the second embodiment of the present disclosure. Referring to FIG. 20, a sensor device 200a includes a lower case 204a, an upper case 210a, and a belt 210b connected to the upper case 210a. A battery case 212 is disposed at one end of the belt 210b and a protrusion is formed on the outside of the belt 210b. On the other hand, a belt hole 210h is formed at the other end of the belt 210b. When the battery case 212 which is a protrusion is inserted into the belt hole 210h, the belt 210b is wound around the grip 10h to be fixed. A fitting member (not illustrated) is disposed on the lower surface of the lower case 204a. Since the fitting member is the same as that in the second example of the embodiment to be described below, the description of the second example will be referred to.

Figure 21:
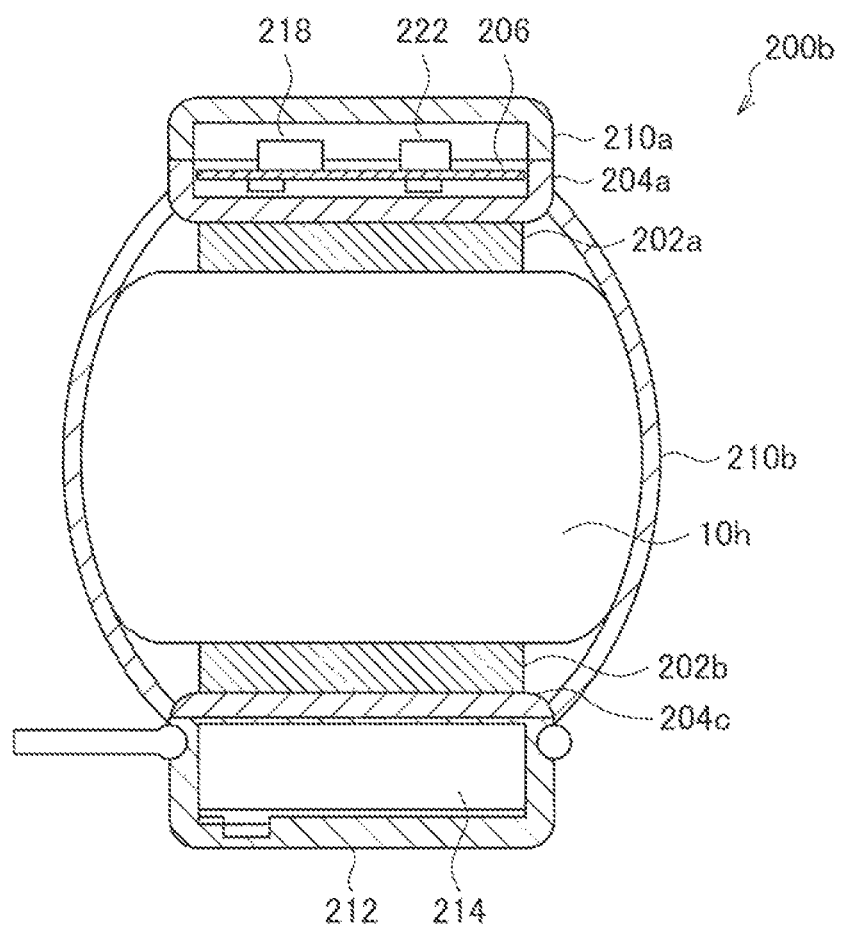
FIG. 21 is a schematic longitudinal sectional view illustrating the first example of the sensor device according to the second embodiment of the present disclosure.
Figure 22:
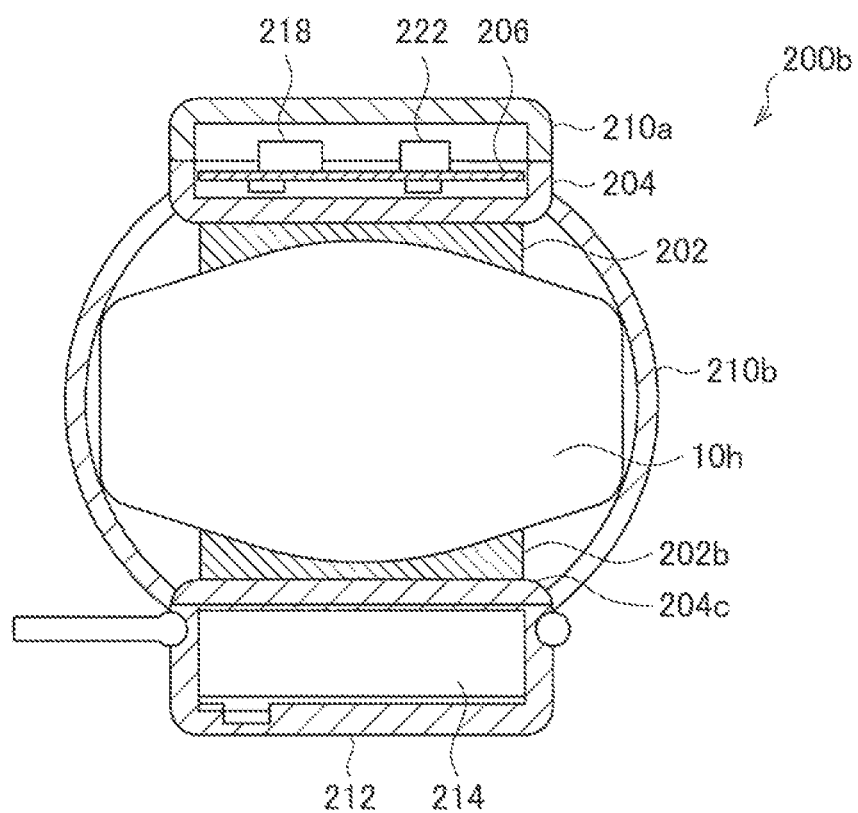
FIG. 22 is a longitudinal sectional view illustrating the first example of the sensor device according to the second embodiment of the present disclosure.

FIGS. 21 and 22 are longitudinal sectional views illustrating the second example of the sensor device according to the second embodiment of the present disclosure. Referring to the drawings, a sensor device 200b includes a lower case 204a and an upper case 210a. A fitting member 202a is disposed on the lower surface of the lower case 204a. The fitting member 202a has a shape corresponding to a fitting surface of the grip 10h. For example, in the example of FIG. 21, since the fitting surface of the grip 10h is flat, the fitting member 202a has a flat surface facing the grip 10h. Since the fitting surface of the grip 10h has a mountain shape in the example of FIG. 22, the fitting member 202a has a valley-shaped surface facing the grip 10h.

Here, as in the fitting member 102 according to the foregoing first embodiment, the fitting member 202a delivers a motion of the racket 10 such as vibration, acceleration, or angular velocity delivered from the grip 10h to the lower case 204a. Therefore, for example, rigid connection can be realized without providing a buffer member such as an elastomer between the fitting member 202a and the lower case 204a. Both of the fitting member 202a and the lower case 204a preferably have materials and shapes for preserving frequency characteristics of vibration which is one of the motions occurring in the racket 10.

A motion of the racket 10 delivered to the lower case 204a is delivered to a sensor substrate 206 joined to the lower case 204a and is detected by a sensor 218 disposed on the sensor substrate 206. In the example illustrated in the drawing, to miniaturize the sensor device 200b, a preprocessing circuit (not illustrated), a communication circuit 222, an antenna (not illustrated), and a control circuit (not illustrated) are integrated along with the sensor 218 on the sensor substrate 206. The upper case 210a is provided on the lower case 204a to protect the sensor 218 and the communication circuit 222 disposed on the sensor substrate 206 against an external impact.

The sensor device 200b includes a belt 204b connected to the lower case 204a. The belt 204b is connected to both sides of the lower case 204a to be wound around the grip 10h and is connected to a facing case 204c on the opposite side with the grip 10h interposed therebetween from the lower case 204a. The battery case 212 is provided in the facing case 204c and the battery 214 can be stored in the battery case 212.

Here, the fitting member 202b having a shape corresponding to the fitting surface of the grip 10h as in the fitting member 202a is also provided in the facing case 204c. Unlike the fitting member 202a delivering a motion of the racket 10 to the sensor 218, the fitting member 202b may attenuate or denature vibration, acceleration, angular velocity, or the like delivered from the grip 10h. For example, to protect the battery 214 stored in the battery case 212 or a circuit connected to the battery 214 from an impact, the fitting member 202b may be connected to the lower case 204c via a buffer member such as an elastomer or the fitting member 202b may be configured as an elastomer.

3. Third Embodiment

Next, a third embodiment of the present disclosure will be described with reference to FIGS. 23 to 25. A sensor device according to the embodiment is fitted on a tennis racket, as in the sensor devices 100 and 200 according to the first and second embodiments, but is different from the sensor devices 100 and 200 in that a fitting position is a shaft portion. Since other details are the same as those of the sensor devices 100 and 200, the repeated description will be omitted below.

Figure 23:
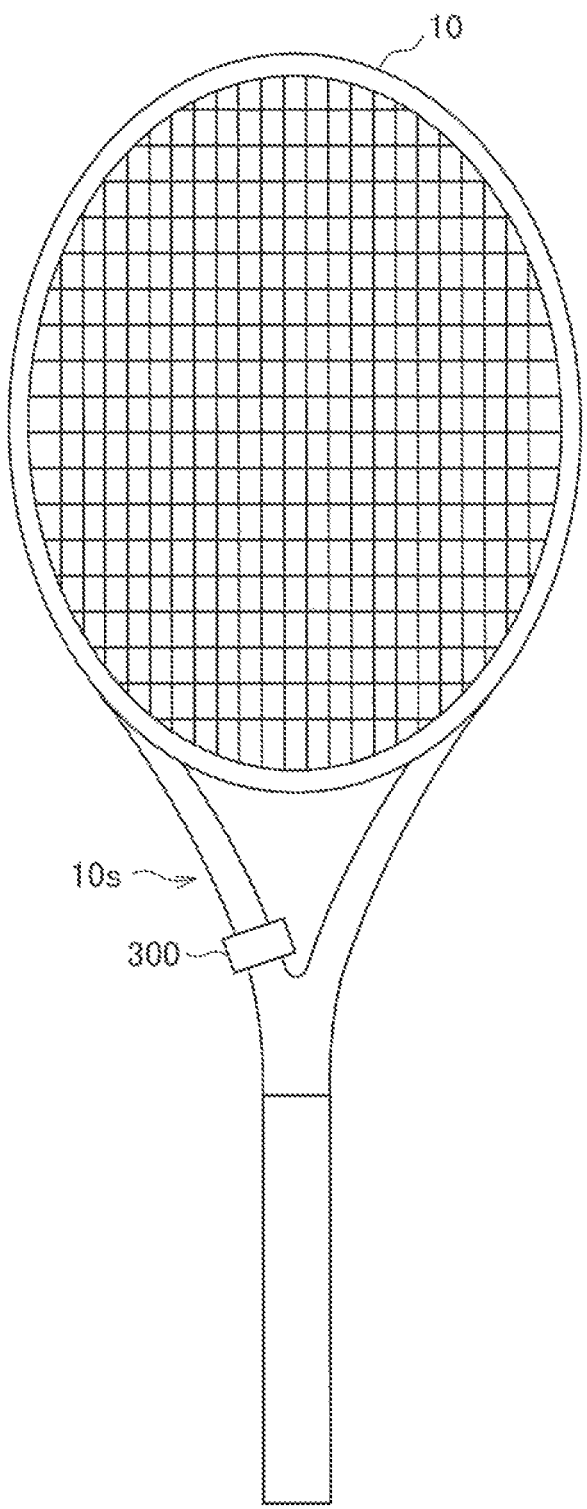
FIG. 23 is an explanatory diagram illustrating a position at which a sensor device is fitted on a hitting tool according to a third embodiment of the present disclosure.

FIG. 23 is an explanatory diagram illustrating a position at which a sensor device is fitted on a hitting tool according to the third embodiment of the present disclosure. In the embodiment, referring to FIG. 23, a sensor device 300 is fitted on a shaft 10s. The sensor device 300 surrounds the shaft 10s and is fixed.

Figure 24:
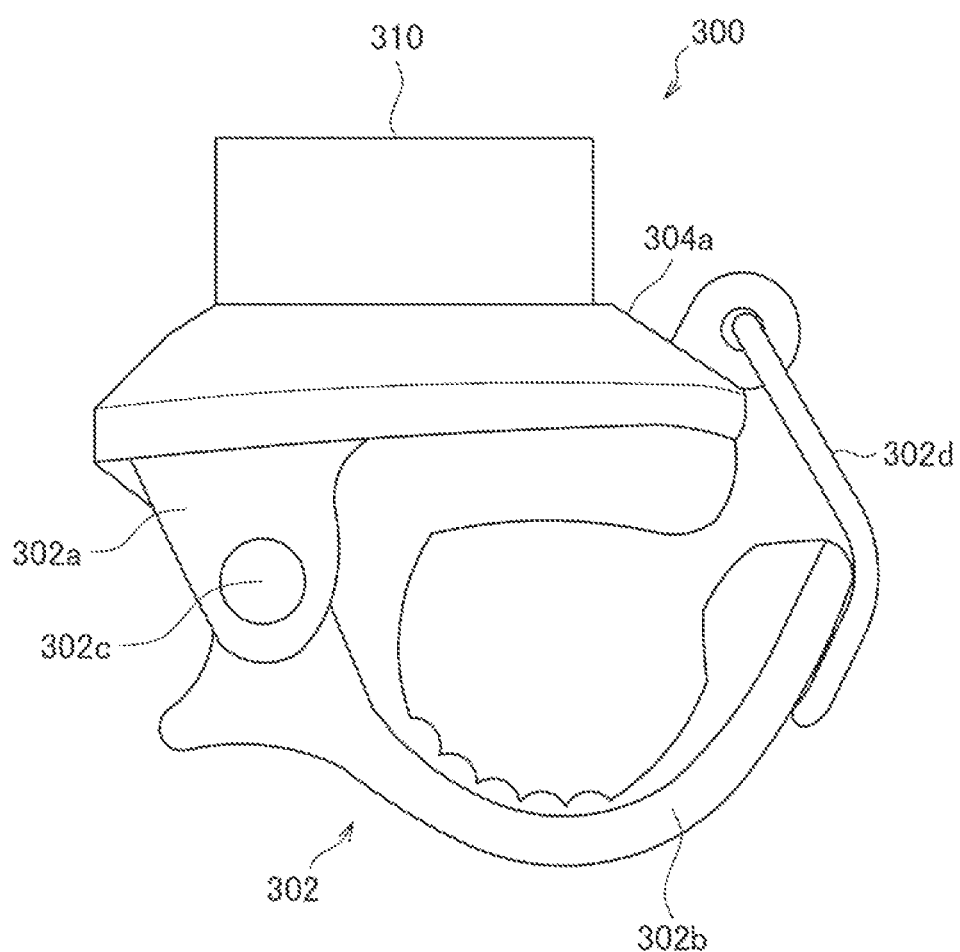
FIG. 24 is a side view illustrating the sensor device according to the third embodiment of the present disclosure.
Figure 25:
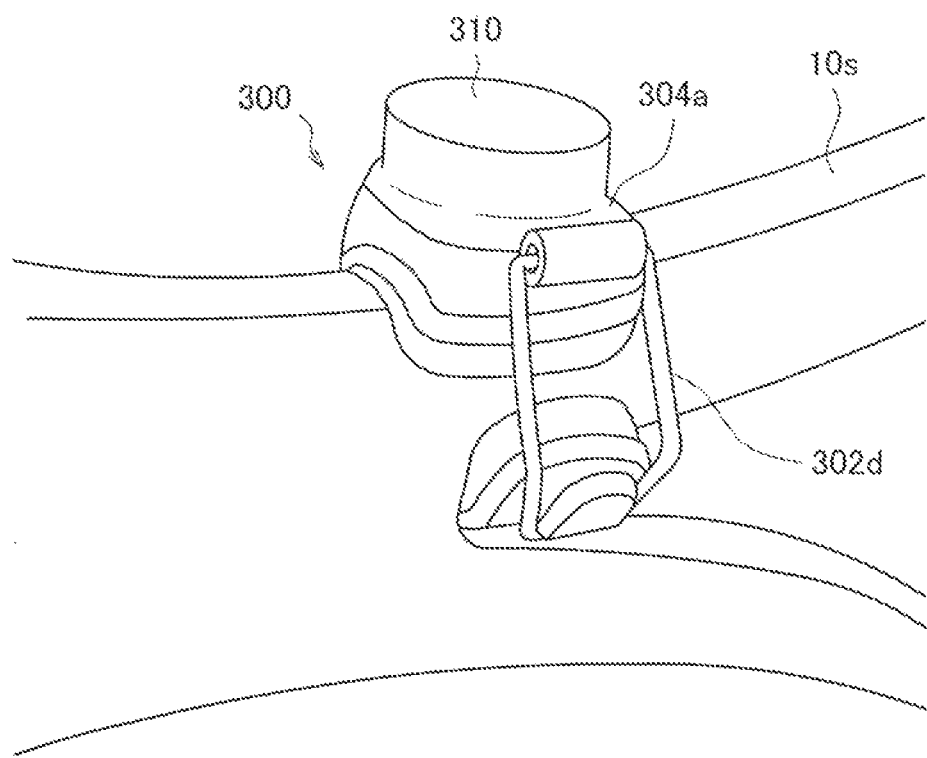
FIG. 25 is a diagram illustrating a state in which the sensor device illustrated in FIG. 24 is fitted.

FIG. 24 is a side view illustrating the sensor device according to the third embodiment of the present disclosure. FIG. 25 is a diagram illustrating a state in which the sensor device illustrated in FIG. 24 is fitted. Referring to the drawing, the sensor device 300 includes a lower case 304, an upper case 310, and a clasp 302 connected to the lower case. The clasp 302 includes a base 302a, an arm 302b, a hinge 302c connecting the base 302a to the arm 302b, and a clip 302d. A sensor substrate, a sensor, a communication circuit, and the like are disposed on the lower case 304 to be protected against an external impact by the upper case 310.

The sensor device 300 is fixed to the racket 10 in such a manner that the clasp 302 holds the shaft 10s of the racket 10 when the clip 302d presses the arm 302b to the inside using an elastic force or the like of a spring. At this time, since the inside surface of the arm 302b and the lower surface of the lower case 304 at least partially come into contact with the shaft 10s to be fixed, a motion such as vibration, acceleration, or angular velocity occurring in the racket 10 is delivered to the clasp 302 and the lower case 304. The delivered motion is delivered to a sensor substrate (not illustrated) via the lower case 304 and is detected by the sensor.

4. Fourth Embodiment

Next, a fourth embodiment of the present disclosure will be described with reference to FIGS. 26 and 27. A sensor device according to the embodiment is fitted on a shaft of a racket, as in the sensor device 300 according to the third embodiment, but is different from the sensor device 300 in a fitting method. Since other details are the same as those of the sensor device 300, the repeated description will be omitted below.

Figure 26:
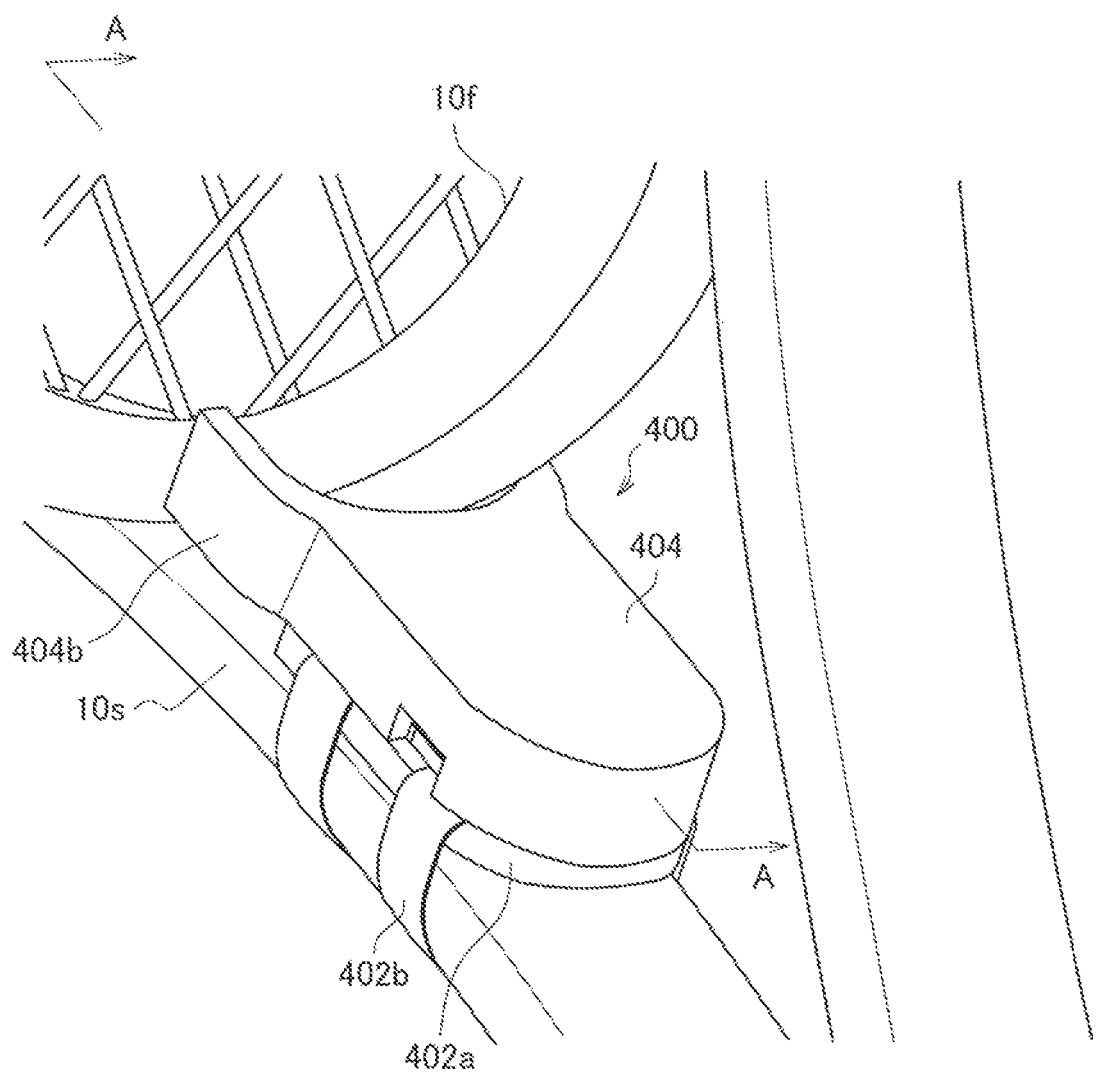
FIG. 26 is a perspective view illustrating a state in which a sensor device is fitted according to a fourth embodiment of the present disclosure.
Figure 27:
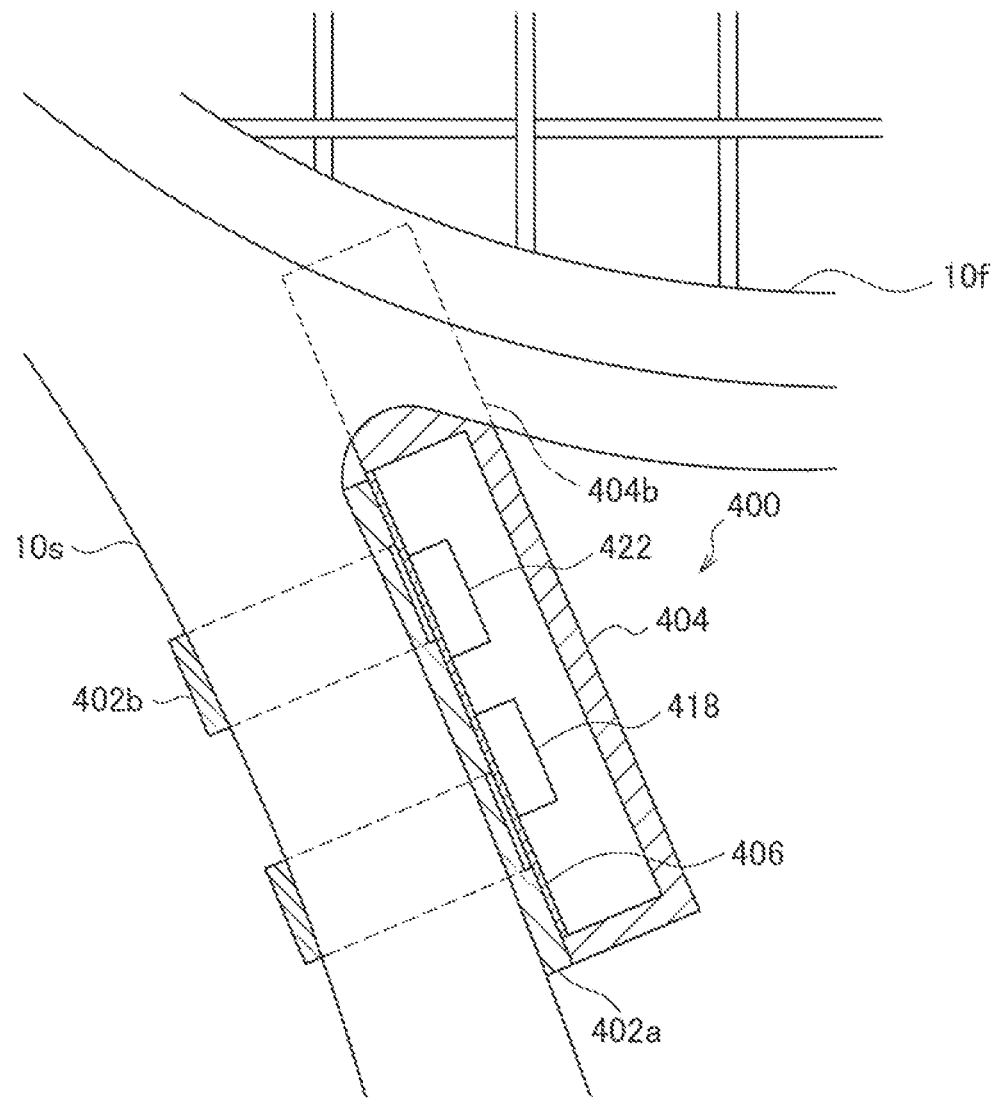
FIG. 27 is a sectional view taken along the line A-A of FIG. 26.

FIG. 26 is a perspective view illustrating a state in which the sensor device is fitted according to the fourth embodiment of the present disclosure. FIG. 27 is a sectional view taken along the line A-A of FIG. 26. Referring to the drawing, a sensor device 400 includes a fitting member 402a and a case 404. The fitting member 402a is fixed to the shaft 10s by a band 402b. The band 402b is wound around the shaft 10s using, for example, a plane fastener.

Here, since the fitting member 402a has a shape corresponding to the surface of the shaft 10s and comes into contact with the shaft 10s to be fixed, a motion such as vibration, acceleration, or angular velocity occurring in the racket 10 is delivered to the fitting member 402a. For example, rigid connection can be realized without providing a buffer member such as an elastomer between the fitting member 402a and the case 404 so that a motion of the racket 10 delivered to the fitting member 402a is delivered to the case 404.

The motion of the racket 10 delivered to the case 404 is delivered to the sensor substrate 406 joined to the case 404 and is detected by a sensor 418 disposed on the sensor substrate 406. In the example illustrated in the drawing, to miniaturize the sensor device 400, a preprocessing circuit (not illustrated), a communication circuit 422, an antenna (not illustrated), and a control circuit (not illustrated) are integrated along with the sensor 418 on the sensor substrate 406. The case 404 coves the sensor substrate 406 and also functions as an exterior member that protects the sensor 418 and the communication circuit 422 disposed on the sensor substrate 406 against an external impact.

On the other hand, a pair of claws 404b are provided in the case 404. As illustrated in the drawing, the claws 404b are provided to surround a frame 10f of the racket 10 when the sensor device 400 is fitted on the shaft 10s. That is, the sensor device 400 is fixed by winding the band 402b around the shaft 10s and is also fixed by the claws 404b surrounding the frame 10f. Thus, the position of the sensor device 400 is not changed even when a centrifugal force (in a direction directed from the shaft 10s to the side of the frame 10f) is received when the racket 10 is swung and the sensor device 400 is also prevented from being rotated with rotation of the shaft 10s.

5. Fifth Embodiment

Next, a fifth embodiment of the present disclosure will be described with reference to FIGS. 28 to 30. A sensor device according to the embodiment is fitted on a shaft of a racket, as in the sensor device 300 according to the third embodiment, but is different from the sensor device 300 in a fitting method. Since other details are the same as those of the sensor device 300, the repeated description will be omitted below.

Figure 28:
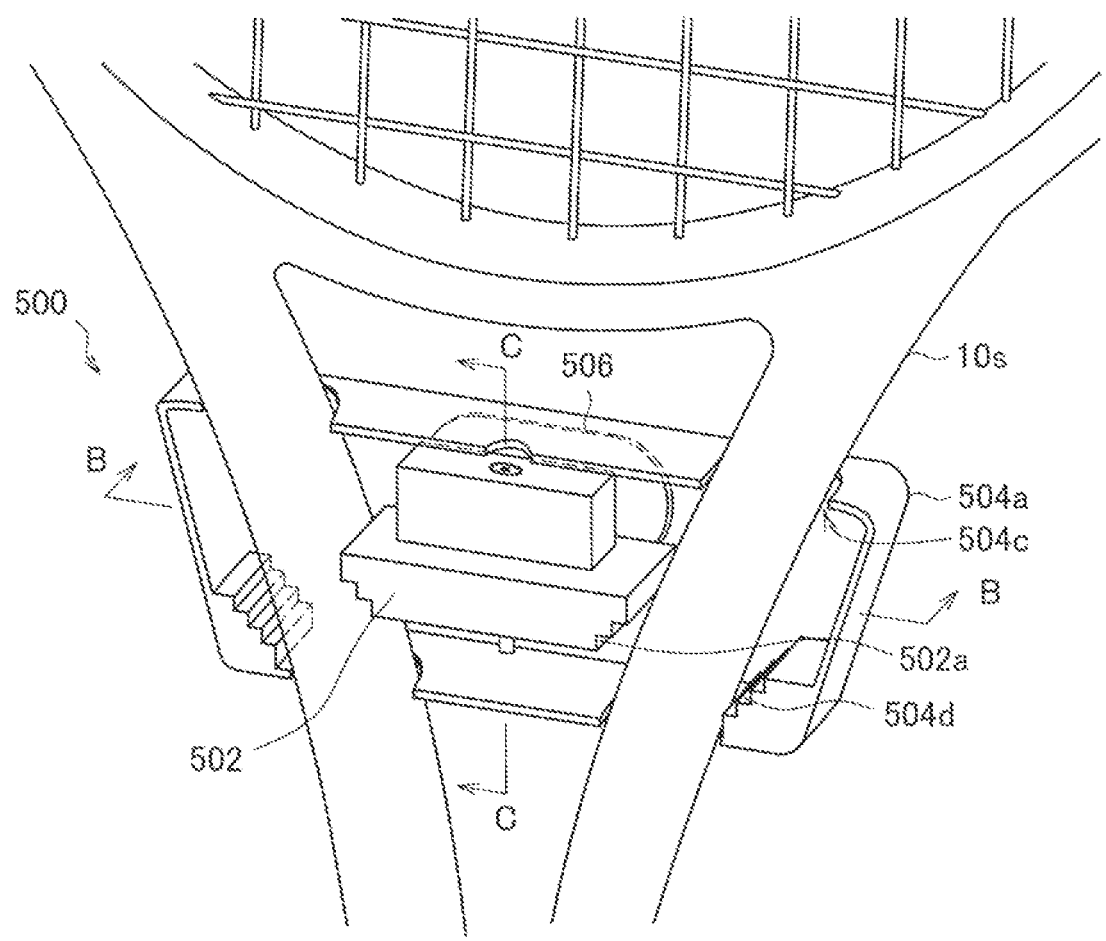
FIG. 28 is a perspective view illustrating a state in which a sensor device is fitted according to a fifth embodiment of the present disclosure.
Figure 29:
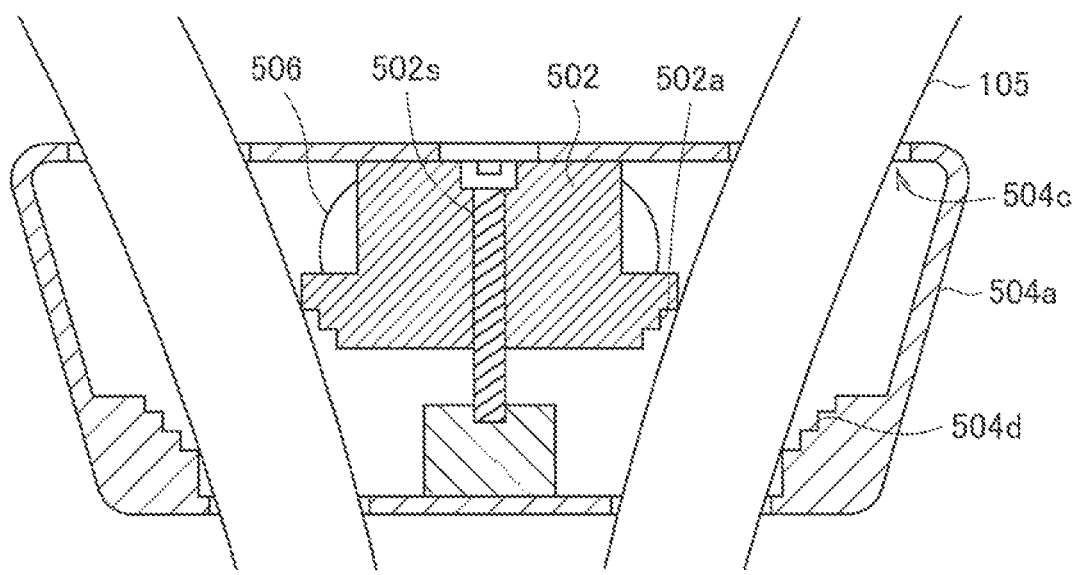
FIG. 29 is a sectional view taken along the line B-B of FIG. 28.

FIG. 28 is a perspective view illustrating a state in which a sensor device is fitted according to a fifth embodiment of the present disclosure. FIG. 29 is a sectional view taken along the line B-B of FIG. 28. FIG. 30 is a sectional view taken along the line C-C of FIG. 28. Referring to the drawing, a sensor device 500 includes a case 504 and a tightening member 502. The perspective view of FIG. 28 illustrates a state in which a part of the case 504 is detached.

Figure 30:
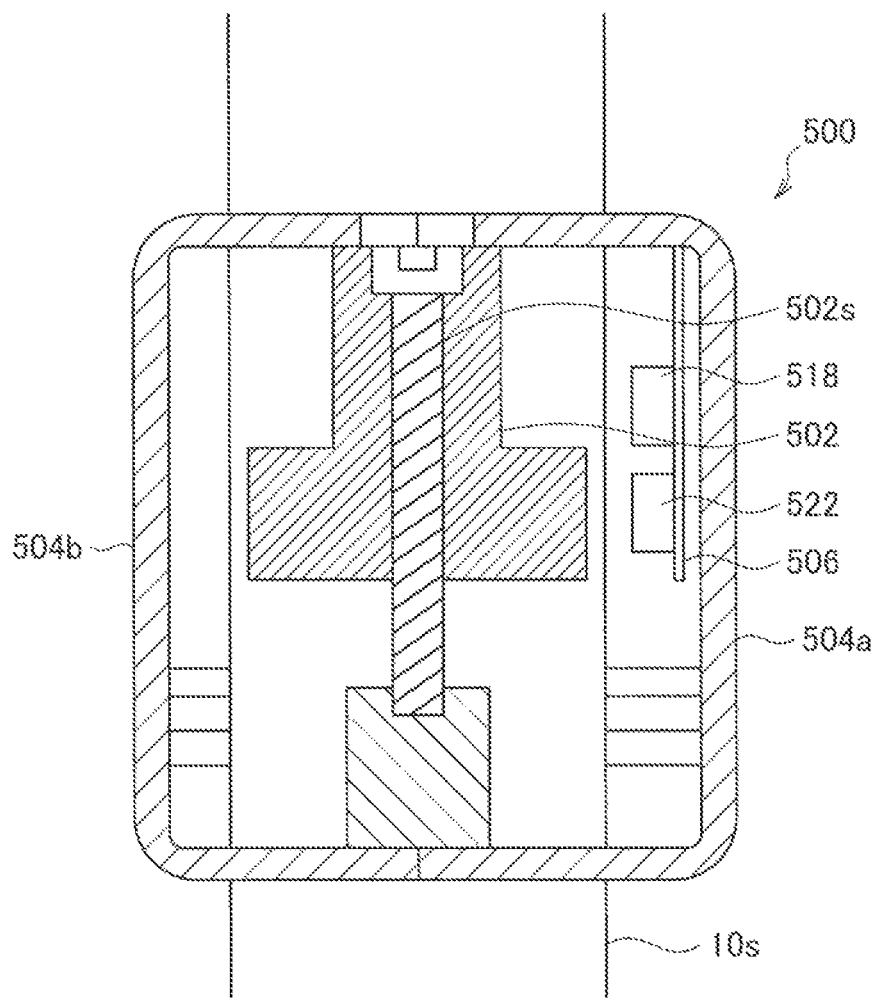
FIG. 30 is a sectional view taken along the line C-C of FIG. 28.

Here, as illustrated particularly in FIG. 30, the case 504 can be separated into cases 504a and 504b in front and rear directions of the racket 10. As illustrated particularly in FIG. 29, the cases 504a and 504b are disposed to pass through penetrated portions 504c corresponding to both of two shafts 10s and are combined to form the case 504.

A step-shaped portion 502d with a shape corresponding to the obliquely penetrating shaft 10s is formed inside the case 504. A similar step-shaped portion 502a is also formed in the tightening member 502 disposed inside the case 504. As illustrated in the drawing, the tightening member 502 tightens the screw 502s to be pressed downward in the drawing when both of the step-shaped portions 502a on both sides face the step-shaped portions 504d of the case 504 with the shaft 10s interposed therebetween. Then, a space between the step-shaped portion 502a of the tightening member 502 and the step-shaped portion 504d of the case 504 is narrowed and the shaft 10s is held between the step-shaped portion 502a and the step-shaped portion 504d, so that the case 504 is fixed to the shaft 10s.

By causing the shapes of the step-shaped portions 504d and 502a to correspond to each other and causing pitches to be partially different (for example, gradually increasing the pitches or conversely decreasing the pitches from the grip to the frame), the case 504 can be fixed to the shaft 10s irrespective of an angle of the shaft 10s obliquely penetrating the case 504 with respect to the case 504 (because certain portions of the step-shaped portions with different pitches can hold the shaft 10s). In such a configuration, a different fitting member may not be prepared depending on the shape of the racket 10. By fixing the sensor device 500 to both of the shafts 10s, it is possible to detect a motion of the racket 10 more precisely.

Since the case 504 is fixed to the shaft 10s by the function of the tightening member 502, a motion such as vibration, acceleration, or angular velocity occurring in the racket 10 is delivered to the case 504. The motion of the racket 10 delivered to the case 504 is delivered to the sensor substrate 506 joined to the case 504 and is detected by the sensor 518 disposed on the sensor substrate 506. In the example illustrated in the drawing, a preprocessing circuit (not illustrated), a communication circuit 522, an antenna (not illustrated), and a control circuit (not illustrated) are integrated along with the sensor 518 on the sensor substrate 506. The case 504 coves the sensor substrate 506 and also functions as an exterior member that protects the sensor 518 and the communication circuit 522 disposed on the sensor substrate 506 against an external impact.

6. Sixth Embodiment

Next, a sixth embodiment of the present disclosure will be described with reference to FIGS. 31 to 33.

Figure 31:
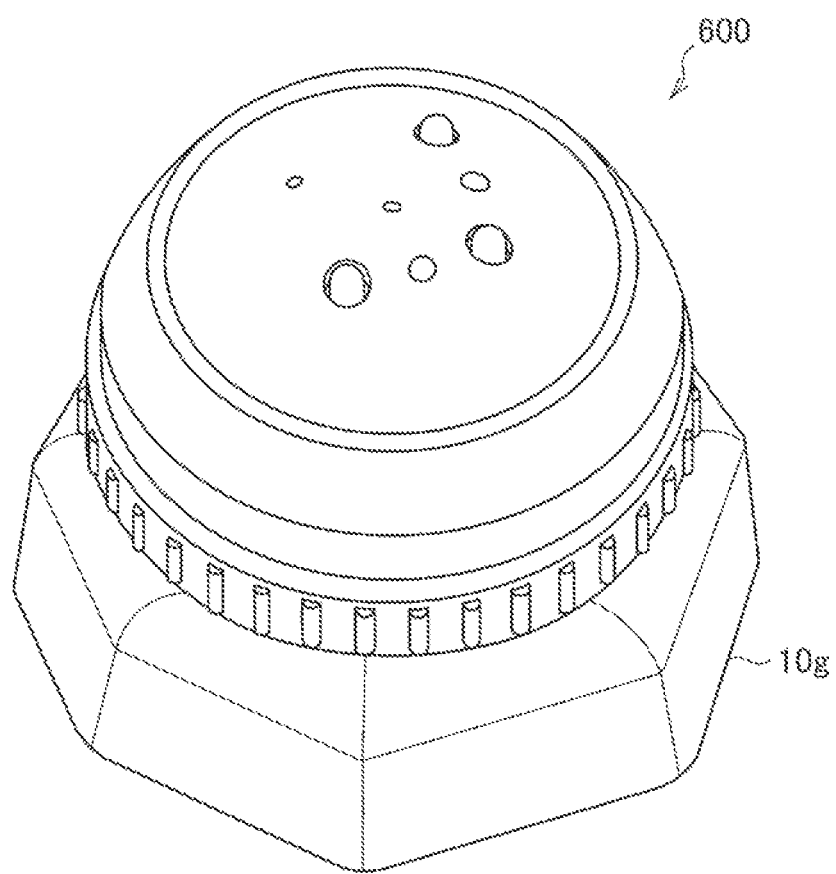
FIG. 31 is an explanatory diagram illustrating a position at which a sensor device is fitted on a hitting tool according to a sixth embodiment of the present disclosure.

FIG. 31 is an explanatory diagram illustrating a position at which a sensor device is fitted on a hitting tool according to a sixth embodiment of the present disclosure. Referring to FIG. 31, a sensor device 600 according to the embodiment is fitted on the grip end 10g of a racket.

FIG. 32 is an explanatory diagram illustrating a schematic configuration of the sensor device according to the sixth embodiment of the present disclosure. FIG. 33 is a sectional view illustrating the sensor device illustrated in FIG. 32.

Figure 33:
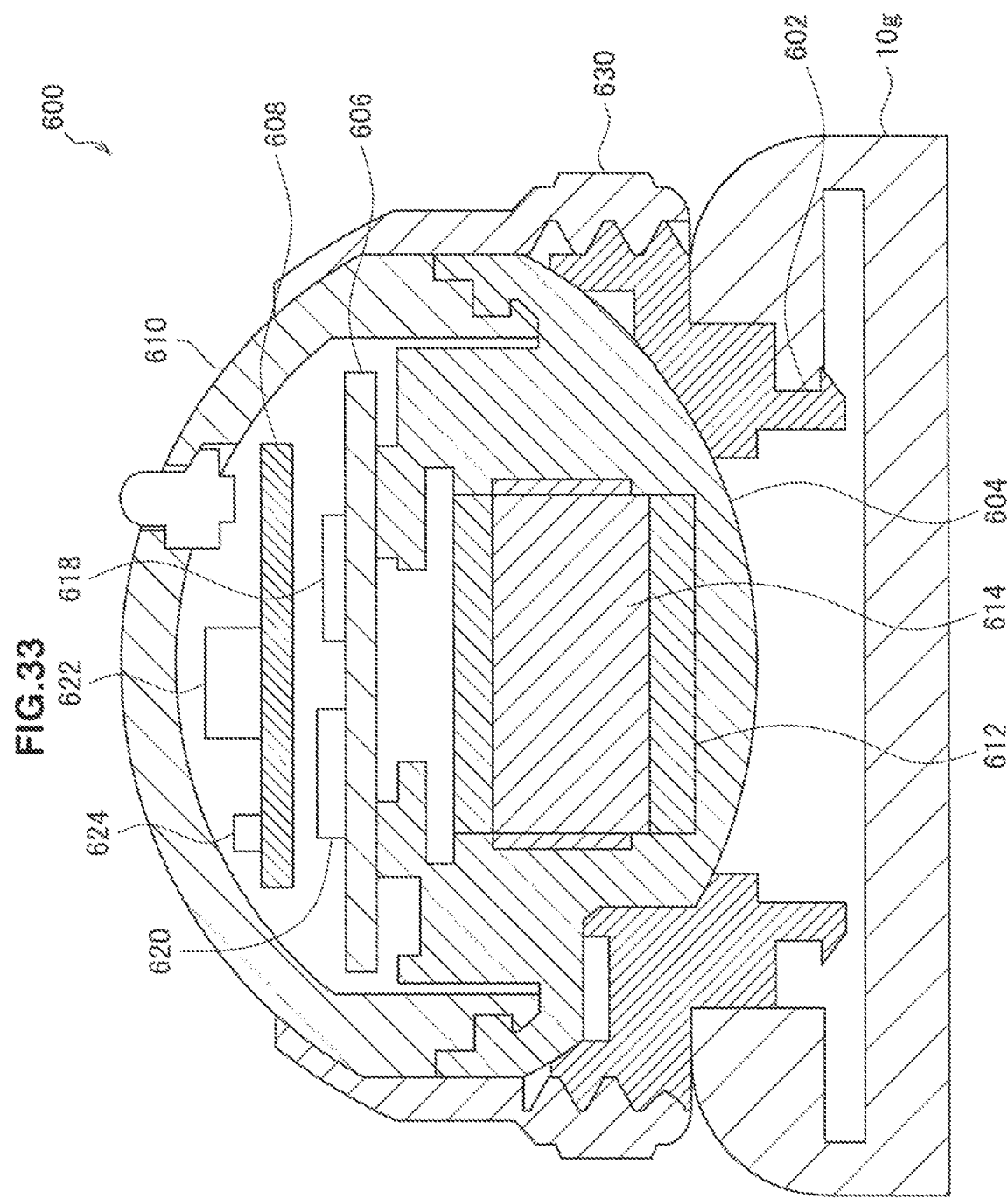
FIG. 33 is a sectional view illustrating the sensor device illustrated in FIG. 32.

Referring to FIGS. 32 and 33, the sensor device 600 includes a fitting member 602, a base member 604, a sensor substrate 606, a communication substrate 608, an exterior member 610, a battery case 612, a battery 614, a sensor 618, a preprocessing circuit 620, a communication circuit 622, an antenna 624, and a screw-attached ring 630. For example, the functions of the members can be the same as those of the fitting member 102, the base member 104, the sensor substrate 106, the communication substrate 108, the exterior member 110, the battery case 112, the battery 114, the sensor 118, the preprocessing circuit 120, the communication circuit 122, the antenna 124, and the screw-attached ring 130 described in the foregoing first embodiment.

In the sensor device 600 according to the embodiment, as illustrated in FIG. 32, a body portion including the base member 604 and the exterior member 610 can be detached from the fitting member 602 and can also be detached from the screw-attached ring 630. Therefore, for example, the body portion can be fitted on a charger with a shape corresponding to the base member 604 to be charged, as in the above-described charger 150, or can be mounted on the fitting member 602 incorporated into another racket or can be mounted on the fitting member 602 fitted on a hitting tool other than a racket. Thus, for example, the sensor device 600 according to the embodiment is different from the sensor device (the screw-attached ring 130 is engaged with the upper surface of the base member 104, and thus is not necessarily a detachably mounted member) described with reference to FIGS. 16 and 17 in that the screw-attached ring 630 is detachably mounted on the base member 604.

7. Seventh Embodiment

Next, a seventh embodiment of the present disclosure will be described with reference to FIGS. 34 and 35.

FIG. 34 is an explanatory diagram illustrating a schematic configuration of a sensor device according to the seventh embodiment of the present disclosure. FIG. 35 is a sectional view illustrating the sensor device illustrated in FIG. 34.

Figure 35:
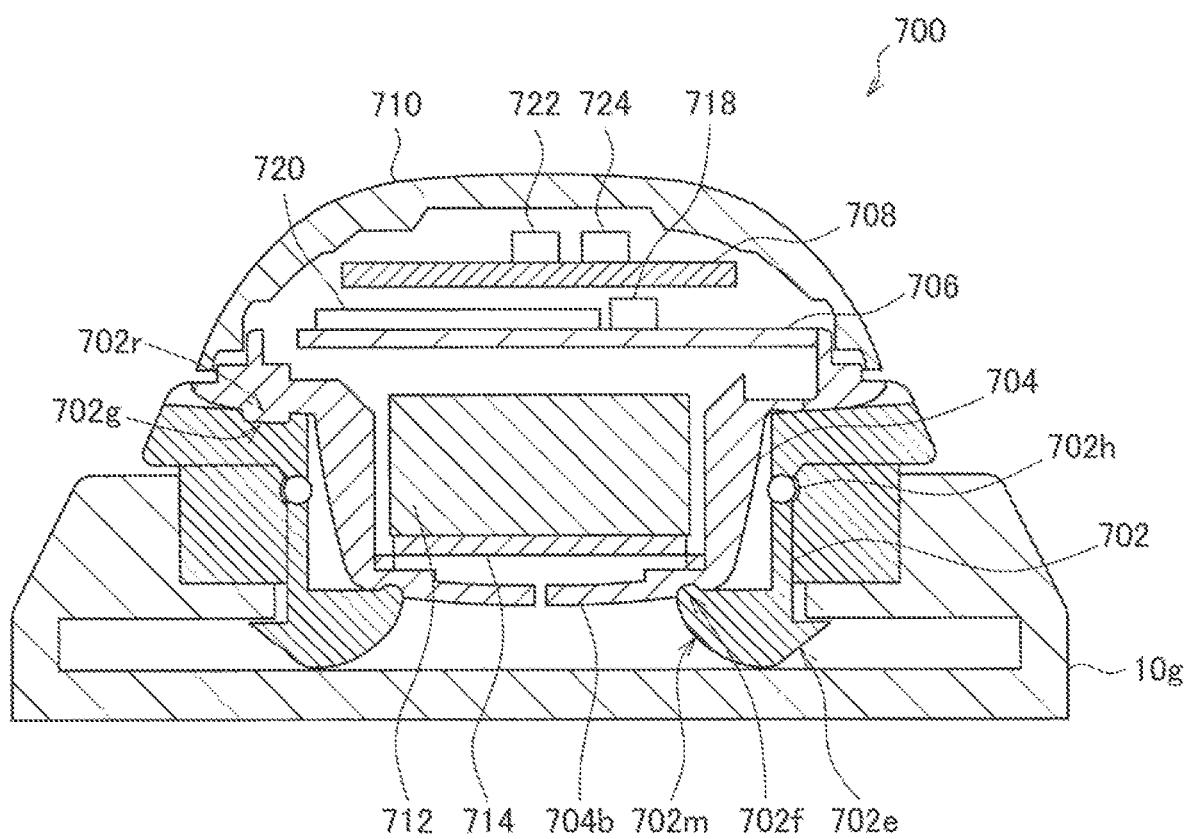
FIG. 35 is a sectional view illustrating the sensor device illustrated in FIG. 34.

Referring to FIGS. 34 and 35, a sensor device 700 includes a fitting member 702 fitted on the grip end 10g of a racket, a base member 704, a sensor substrate 706, a communication substrate 708, an exterior member 710, a battery case 712, a battery 714, a sensor 718, a preprocessing circuit 720, a communication circuit 722, and an antenna 724. For example, the functions of the members can be the same as those of the fitting member 102, the base member 104, the sensor substrate 106, the communication substrate 108, the exterior member 110, the battery case 112, the battery 114, the sensor 118, the preprocessing circuit 120, the communication circuit 122, and the antenna 124 described in the foregoing first embodiment.

Here, the fitting member 702 includes a claw 702e that engages with a groove inside the grip end 10g and functions as a latch. The fitting member 702 strongly locks in the grip end 10g through an operation of the claw 702e and the body portion on the base member 704 is mounted on the fitting member 702 so that, for example, impact resistance of the sensor device 700 in a surface fitted state can be improved.

As illustrated in the drawing, an arm portion 702m including the claw 702e in the fitting member 702 is connected to another portion (a portion including the upper surface facing the base member 704) via a hinge 702h. The arm portion 702m is rotatable about the hinge 702h. Accordingly, for example, when the arm portion 702m is rotated toward the center side of the grip, the engagement of the claw 702e and the groove of the grip end 10g is released and the fitting member 702 can be detached from the grip end 10g.

Accordingly, for example, when the base member 704 is not mounted, a user rotates the arm portion 702m of the fitting member 702 toward the center side of the grip with his or her finger or the like (performs an operation of raising the arm portion 702m to the inside) and the arm portion 702m is urged toward the center side of the grip by an urging unit such as a separately provided spring, so that the engagement of the claw 702e and the groove of the grip end 10g can be released and the fitting member 702 can be easily detached from the grip end 10g.

Thus, when the fitting member 702 can be fitted in or removed from the grip end 10g regardless of elastic deformation, it is not necessary to apply a considerable force to the fitting member 702 at the time of the fitting or the removing. Thus, any user can fit the fitting member 702 in the racket 10 or readily replace the fitting member 702. The durability of the fitting member 702 can be improved since the elastic deformation is not necessary, and the grip end 10g can also be prevented from being damaged or deformed due to an excessively applied load.

In the arm portion 702m of the fitting member 702, a protrusion 702f is formed on the center side of the grip on the opposite side of the claw 702e. The protrusion 702f comes into contact with a bottom surface 704b of the base member 704 when the claw 702e engages with the groove of the grip end 10g. Accordingly, when the claw 702e does not engage with the groove of the grip end 10g and a protrusion 704a of the base member 704 is inserted into an opening 702a, the protrusion 702f comes into contact with the bottom surface 704b during the insertion to be pushed down. Thereafter, the arm portion 702m is rotated toward the outside of the grip about the hinge 702h, so that the claw 702e consequently engages with the groove of the grip end 10g.

Here, as illustrated in FIG. 34, an uneven portion may be formed on the bottom surface 704b of the base member 704. In this case, by inserting the protrusion 704a into the opening 702a and subsequently rotating the base member 704 so that a convex portion of the uneven portion of the bottom surface 704b comes into contact with the protrusion 702f of the fitting member 702, it is possible to push the protrusion 702f down and engage the claw 702e with the groove of the grip end 10g. For example, when a step is attached to the uneven portion formed on the bottom surface 704b to adjust how much the protrusion 702f is pushed down, the depth of the claw 702e that enters the grip end 10g can also be adjusted. Thus, a difference in the shape of the individual racket 10 can be absorbed and the fitting member 702 can be fitted.

A rib 704r protruding toward the facing fitting member 702 is formed on the bottom surface of the base member 704. On the other hand, a groove 702g corresponding to the rib 704r is formed on the upper surface of the fitting member 702. For example, the rib 704r and the groove 702g function like the rib 104r and the groove 102g in the above-described first embodiment and provide line contact or point contact between the base member 704 and the fitting member 702, so that rattling can be suppressed and a motion of the racket 10 can be delivered from the fitting member 102 to the base member 104 by stable junction.

8. Eighth Embodiment

Next, an eighth embodiment of the present disclosure will be described with reference to FIGS. 36 and 37.

Figure 36:
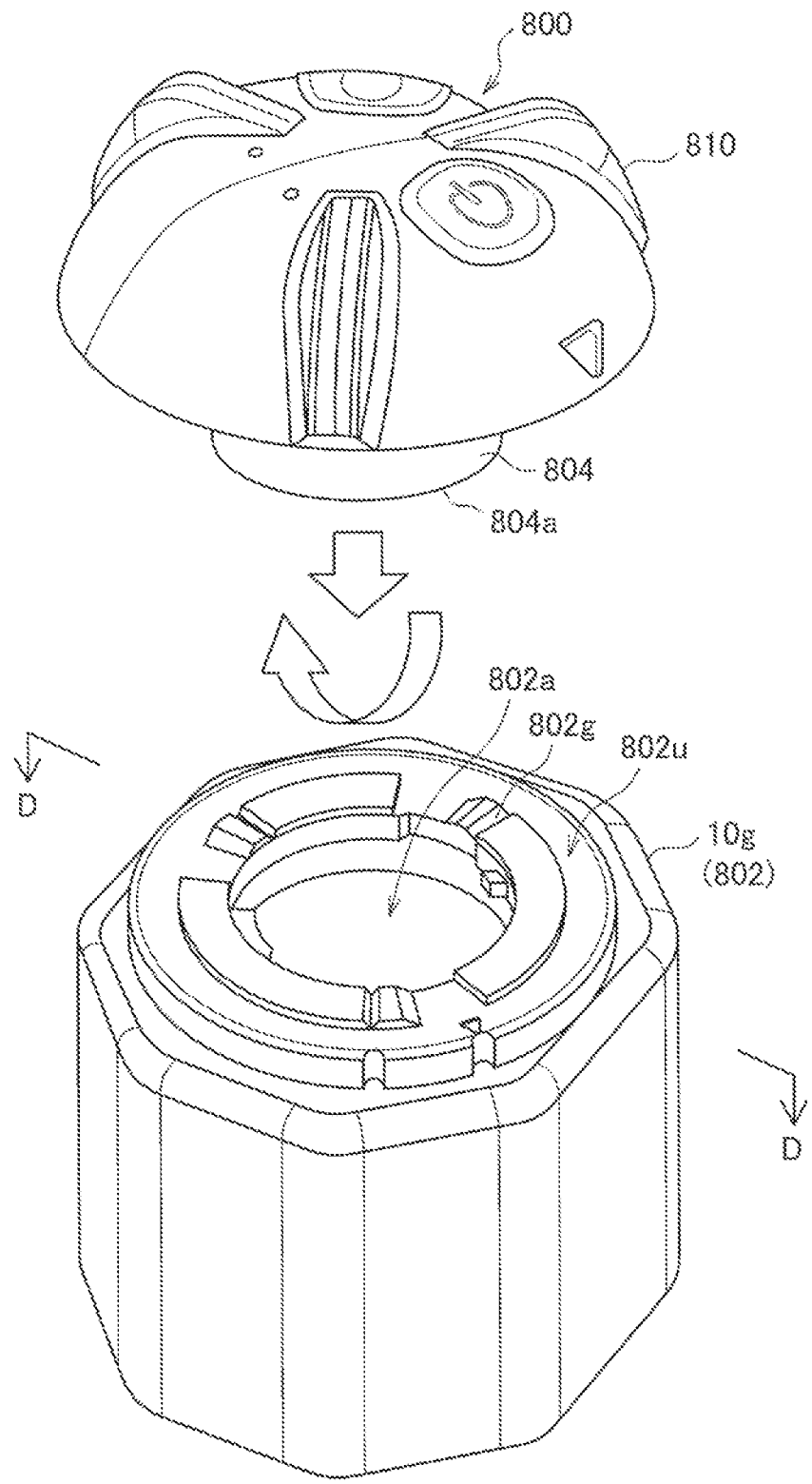
FIG. 36 is an explanatory diagram illustrating a schematic configuration of a sensor device and a grip end according to an eighth embodiment of the present disclosure.

FIG. 36 is an explanatory diagram illustrating a schematic configuration of a sensor device and a grip end according to the eighth embodiment of the present disclosure. FIG. 37 is a sectional view illustrating a grip end taken along the line D-D of FIG. 36.

Figure 37:
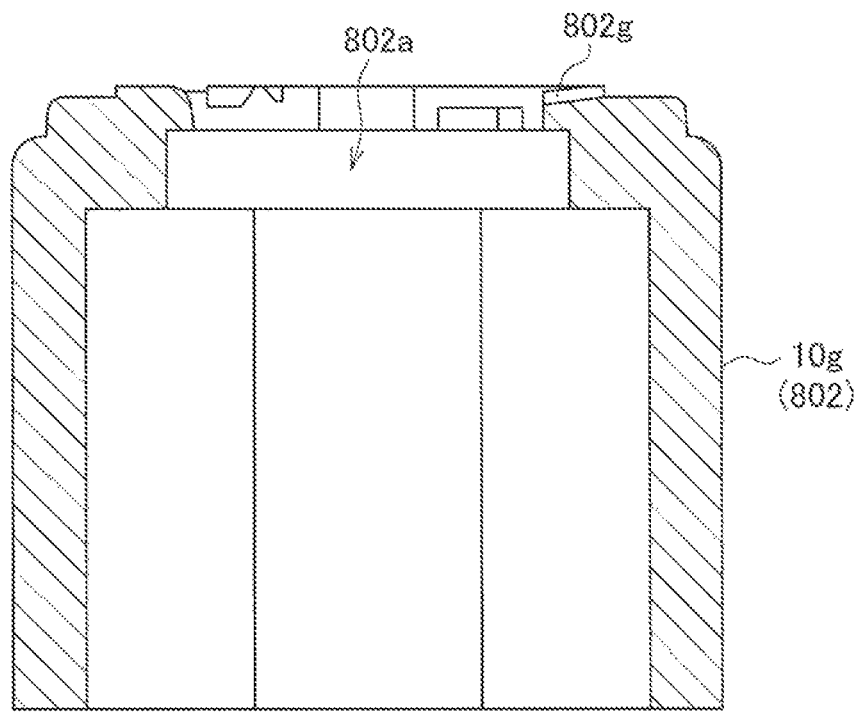
FIG. 37 is a sectional view illustrating the grip end taken along the line D-D of FIG. 36.

Referring to FIGS. 36 and 37, a sensor device 800 includes a base member 804 and an exterior member 810. For example, a sensor device 800 has the same configuration as the sensor device 100 described in the foregoing first embodiment except that a fitting structure 802 is integrated with the grip end 10g. Therefore, the detailed descriptions other than that of the fitting structure 802 (the grip end 10g) will be omitted.

In the embodiment, a relation between the fitting structure 802 and the base member 804 can be the same as, for example, the relation between the fitting member 102 and the base member 104 of the sensor device 100 according to the foregoing first embodiment. More specifically, for example, an opening 802a is formed in an upper surface 802u of the fitting structure 802, and thus a protrusion 804a formed on the lower surface of the base member 804 is inserted into the opening 802a so that the base member 804 is mounted on the fitting structure 802. Here, since the fitting structure 802 is integrated with the grip end 10g, mounting of the sensor device 800 on the grip end 10g is completed by mounting the base member 804 on the fitting member 802.

The fitting structure 802 can include, for example, a configuration related to a junction with the base member 804, as in the fitting member 102 described in the first embodiment. For example, a groove 802g into which a rib (not illustrated) formed in the lower surface of the base member 804 is thrust may be formed in the upper surface of the fitting structure 802. Since the fitting structure 802 is integrated with the grip end 10g, the fitting structure 802 does not have, for example, a configuration for joining the grip end 10g and the fitting member 102 described in the first embodiment, more specifically, the configuration of the claw 102h.

In the configuration described above in the embodiment, that is, in the configuration in which the fitting structure 802 is integrated with the grip end 10g, there is no junction structure between the fitting structure 802 and the grip end 10g. Therefore, a protrusion height from the grip end 10g when the sensor device 800 is fitted can be suppressed. Further, since the fitting structure 802 need not be separately manufactured, it is possible to reduce cost occurring due to an increase in the number of members. Since there is no junction structure between the fitting structure 802 and the grip end 10g, it is possible to improve rigidity of a fitting portion of the sensor device 800. Since the number of junction portions decreases from two (between the grip end and the fitting structure and between the fitting structure and the base member) to one (between the fitting structure and the base member), it is possible to reduce noise mixed in vibration data detected in the sensor device 800.

9. Ninth Embodiment

Next, a ninth embodiment of the present disclosure will be described with reference to FIGS. 38 to 41.

Figure 38:
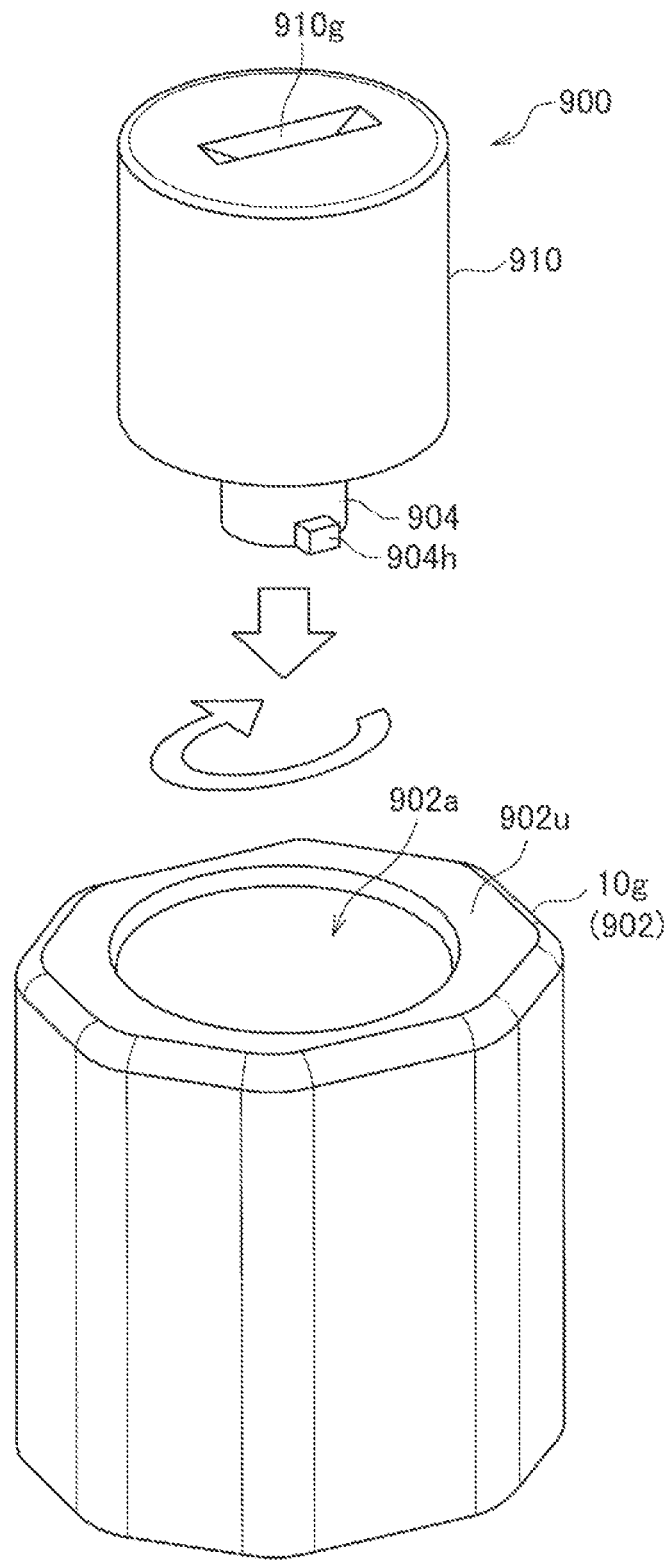
FIG. 38 is an explanatory diagram illustrating a schematic configuration of a sensor device and a grip end according to a ninth embodiment of the present disclosure.
Figure 39:
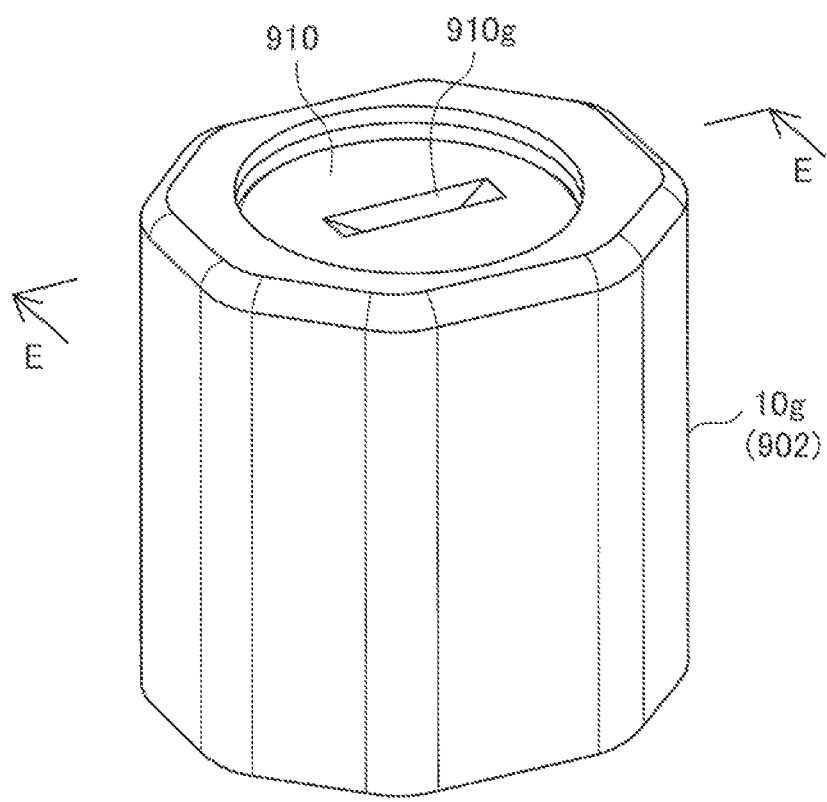
FIG. 39 is an explanatory diagram illustrating a schematic configuration of a sensor device and a grip end according to the ninth embodiment of the present disclosure.
Figure 40:
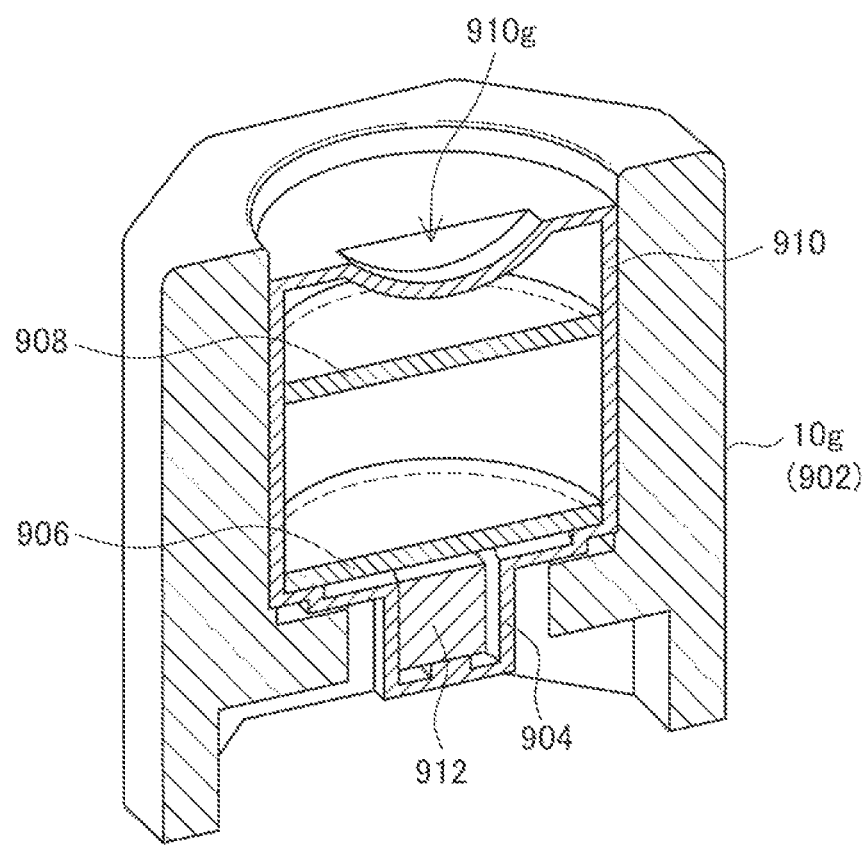
FIG. 40 is a sectional view illustrating the sensor device and the grip end taken along the line E-E of FIG. 39.

FIGS. 38 and 39 are explanatory diagrams illustrating a schematic configuration of a sensor device and a grip end according to the ninth embodiment of the present disclosure. FIG. 38 illustrates a state before mounting and FIG. 39 illustrates a state after mounting. FIG. 40 is a sectional view illustrating the sensor device and the grip end taken along the line E-E of FIG. 39. FIG. 41 is an explanatory diagram illustrating a junction structure between a fitting structure and a base member of the sensor device according to the ninth embodiment of the present disclosure.

Referring to the foregoing drawings, the sensor device 900 includes a base member 904, a sensor substrate 906, a communication substrate 908, an exterior member 910, and a battery case 912. The sensor device 900 has the same configuration as the sensor device 100 described in the foregoing first embodiment except that the fitting structure 902 is integrated with the grip end 10g and the body portion including the base member 904 can be accommodated in the grip end 10g. Therefore, the detailed description other than that of a fitting structure 902 (the grip end 10g) and members (the base member 904 and the exterior member 910) forming an external shape will be omitted.

An opening 902a is formed in an upper surface 902u of the fitting structure 902 and the sensor device 900 is mounted on the grip end 10g by accommodating the body portions of the sensor device 900 including the base member 904 in the opening 902a. As illustrated particularly in FIG. 41, by inserting the sensor device 900 into the opening 902a and subsequently rotating the sensor device 900 about the axis of the grip end 10g, a claw 904h formed in the base member 904 engages with a claw 902h formed in the fitting structure 902, so that the base member 904 is fixed to the fitting structure 902.

At this time, in order to easily rotate the body portion of the sensor device 900 inside the opening 902a, a groove 910g may be formed in the exterior member 910. By inserting a jig (including a case in which a coin or the like is used instead of a jig) into the groove 910g, the body portion can be easily rotated even after the body portion of the sensor device 900 is accommodated in the opening 902a. A rib 904r may be formed on the lower surface of the base member 904 and a groove 902g may be formed inside the fitting structure 902 and on the bottom surface of the opening 902a, so that the fitting structure 902 and the base member 904 can be strongly joined by point contact or line contact.

In the configuration described above in the embodiment, that is, in the configuration in which the fitting structure 902 is integrated with the grip end 10g and the entire sensor device 900 (the portion including the base member 904) is accommodated inside the grip end 10g through the opening 902a formed in the fitting structure 902, for example, a protrusion height from the grip end 10g when the sensor device 900 is fitted can be suppressed more than in the foregoing eighth embodiment (for example, the protrusion can be removed).

As in the foregoing eighth embodiment, since the fitting structure 902 is not separately manufactured, it is possible to reduce cost occurring due to an increase in the number of members. Further, since there is no junction structure between the fitting structure 902 and the grip end 10g, the rigidity of the fitting portion of the sensor device 900 can be improved. Further, since the number of junction portions is decreased from two to one, it is also possible to reduce noise mixed in the vibration data detected in the sensor device 900.

10. Tenth Embodiment

Next, a tenth embodiment of the present disclosure will be described with reference to FIG. 42. FIG. 42 is a sectional view illustrating a schematic configuration of a sensor device and a grip end according to the tenth embodiment of the present disclosure.

Referring to FIG. 42, a sensor device 1000 includes a base member 1004, a sensor substrate 1006, a communication substrate 1008, an exterior member 1010, and a battery case 1012. The sensor device 1000 has the same configuration as the sensor device 900 according to the foregoing ninth embodiment except that members (claws 1004h, a spring 1004s, grooves 1010g, and a knob 1010k) for engaging the base member 1004 and with the fitting structure 1002 are formed, as will be described below. Therefore, the detailed description of details other than these will be omitted.

In the embodiment, when the knob 1010k takes in and out in the axial direction of the grip end 10g, the claws 1004h are opened and closed through an operation of the spring 1004s provided in the base member 1004. As illustrated in FIG. 42, a state in which the knob 1010k is pushed is a locked state. The claws 1004h are opened to engage with claws 1002h formed in the fitting structure 1002, so that the body portion of the sensor device 1000 is fixed to the fitting structure 1002. On the other hand, when a user of the sensor device 1000 pulls the knob 1010k, the claws 1004h are closed and the engagement with the claws 1002h is released, so that the locked state becomes an unlocked state. The grooves 1010g accommodate protrusion portions of the knob 1010k at positions corresponding to the locked state and the unlocked state to maintain the position of the knob 1010k.

In the configuration described above in the embodiment, that is, in the configuration in which the fitting structure 1002 is integrated with the grip end 10g, the entire sensor device 1000 is accommodated inside the grip end 10g, and the knob 1010k changing the engagement state of the fitting structure 1002 and the base member 1004 is further formed, the sensor device 1000 can be mounted on the grip end 10g even when a jig is not used, for example, in addition to the advantages obtained in the foregoing ninth embodiment. For example, it is possible to easily recognize the fitting state of the sensor device 1000 on the grip end 10g visually in accordance with the knob 1010k.

11. Supplement

Preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)

A sensor device including:

a base member configured to be mounted on a hitting tool via a fitting structure;

a substrate joined to the base member;

a sensor disposed on the substrate and configured to detect a motion of the hitting tool delivered via the base member and the substrate;

a communication unit configured to transmit a detection result of the motion of the hitting tool to an external device; and an exterior member configured to cover the sensor and the communication unit.

(2)

The sensor device according to (1), wherein the fitting structure is formed by a fitting member independent from the hitting tool, wherein the sensor device further includes the fitting member, wherein the fitting member has a shape corresponding to a shape of a fitting portion of the hitting tool, and wherein the base member is detachably mounted on the fitting member.

(3)

The sensor device according to (2), wherein the fitting member has a shape which is able to fit into a grip end of the hitting tool.

(4)

The sensor device according to (3), wherein the fitting member includes an octagonal pillar portion which is able to fit into the grip end, and wherein the base member includes a cylindrical protrusion that fits into the octagonal pillar portion and a battery case internally included in the protrusion.

(5)

The sensor device according to (4), wherein the communication unit is disposed on an opposite side to the battery case with the base member and the substrate interposed between the communication unit and the battery case.

(6)

The sensor device according to (3), wherein the fitting member includes an arm portion configured to be rotatable with respect to a portion facing the base member, a claw formed in the arm portion and configured to engage with an inside portion of the grip end when the arm portion is rotated in a first direction, and a protrusion formed in the arm portion and configured to come into contact with the base member when the base member is mounted on the fitting member, to rotate the arm portion in the first direction.

(7)

The sensor device according to (6), wherein the engagement of the claw and the inside portion of the grip end is released by rotating the arm portion in a second direction opposite to the first direction.

(8)

The sensor device according to any one of (2) to (7), wherein the base member comes into line contact or point contact with the fitting member.

(9)

The sensor device according to any one of (2) to (8), wherein the base member further includes a lock mechanism that locks a positional relation between the base member and the fitting member when the base member is mounted on the fitting member.

(10)

The sensor device according to (2), wherein the fitting member has a shape capable of holding a shaft-shaped portion of the hitting tool, and wherein the base member is mounted on the fitting member.

(11)

The sensor device according to (2), wherein the fitting member and the base member have mutually corresponding shapes capable of holding a shaft-shaped portion of the hitting tool, and wherein the base member is fitted on the hitting tool by holding the shaft-shaped portion between the base member and the fitting member.

(12)

The sensor device according to (1), wherein the fitting structure is integrated with the hitting tool.

(13)

The sensor device according to (12), wherein a portion including the base member is accommodated inside the hitting tool through an opening formed in the fitting structure.

(14)

The sensor device according to (13), wherein the portion including the base member is rotated inside the opening to be fixed to the fitting structure.

(15)

The sensor device according to (14), wherein, in the exterior member, a groove through which a jig for rotating the portion including the base member is inserted is formed.

(16)

The sensor device according to (13), wherein the base member further includes a claw that is able to be opened and closed inside the opening, and wherein the portion including the base member is fixed to the fitting structure by the claw.

(17)

The sensor device according to any one of (1) to (16), wherein the exterior member has a structure that protects the sensor and the communication unit from an external impact.

(18)

The sensor device according to (17), wherein spaces are formed between the exterior member and the sensor, and between the exterior member and the communication unit.

(19)

The sensor device according to any one of (1) to (18), wherein the base member is detachably mounted on the fitting member and is detachably mounted on a charger that has a shape corresponding to a mounting portion of the base member, and wherein the sensor device further includes a battery case, and a connection terminal configured to connect a battery accommodated in the battery case to a charging terminal of the charger when the base member is mounted on the charger.

(20)

The sensor device according to any one of (1) to (19), wherein the base member and the exterior member are connected by a waterproof structure.

(21)

The sensor device according to any one of (1) to (20), wherein the base member and the substrate have materials and shapes that preserve frequency characteristics of delivered vibration of the hitting tool.

(22)

The sensor device according to any one of (1) to (21), wherein the sensor includes two sensors with mutually different detection directions.

(23)

The sensor device according to (22), wherein the detection directions of the two sensors are orthogonal.

(24)

The sensor device according to (23), wherein the detection directions of the two sensors include a first direction parallel to a hitting plane of the hitting tool and a second direction at right angles to the hitting plane.

(25)

The sensor device according to any one of (1) to (24), wherein the base member and the exterior member are integrally formed.

REFERENCE SIGNS LIST 100, 200, 300, 400, 500 sensor device
102, 202a, 402a fitting member
104 base member
106, 206, 406, 506 sensor substrate
108 communication substrate
110 exterior member
112, 212 battery case
114, 214 battery
116 lock mechanism
118, 218, 418, 518 sensor
122, 222, 422, 522 communication circuit
134 connection terminal
150 charger
154 charging terminal
204a, 304, 404 lower case
210a, 310 upper case
302 clasp
502 tightening member

The invention claimed is:

1. A sensor device comprising:
a fitting member independent from a hitting tool;
a base member configured to be mounted on the hitting tool via the fitting member;
a substrate joined to the base member;
a sensor disposed on the substrate and configured to detect a motion of the hitting tool delivered via the base member and the substrate;
a communication unit configured to transmit a detection result of the motion of the hitting tool to an external device;
an exterior member configured to cover the sensor and the communication unit,
wherein the fitting member includes a shape which is able to fit into a grip end of the hitting tool and corresponds to a shape of a fitting portion of the hitting tool,
wherein the base member is detachably mounted on the fitting member, and
wherein the base member further includes a lock mechanism that locks a positional relation between the base member and the fitting member when the base member is mounted on the fitting member;
an arm portion configured to be rotatable with respect to a portion facing the base member;
a claw formed in the arm portion and configured to engage with an inside portion of the grip end when the arm portion is rotated in a first direction; and
a protrusion formed in the arm portion and configured to come into contact with the base member when the base member is mounted on the fitting member, to rotate the arm portion in the first direction.

2. The sensor device according to claim 1,
wherein the base member is detachably mounted on the fitting member and is detachably mounted on a charger that has a shape corresponding to a mounting portion of the base member, and
wherein the sensor device further includes:
a battery case; and
a connection terminal configured to connect a battery accommodated in the battery case to a charging terminal of the charger when the base member is mounted on the charger.

3. The sensor device according to claim 2,
wherein the fitting member includes an octagonal pillar portion which is able to fit into the grip end, and
wherein the base member includes a cylindrical protrusion that fits into the octagonal pillar portion and a battery case internally included in the protrusion.

4. The sensor device according to claim 3,
wherein the base member comes into line contact or point contact with the fitting member.

5. The sensor device according to claim 1, wherein the exterior member has a structure that protects the sensor and the communication unit from an external impact.

6. The sensor device according to claim 1, wherein the base member and the substrate have materials and shapes that preserve frequency characteristics of delivered vibration of the hitting tool.

7. The sensor device according to claim 1, wherein the sensor includes two sensors with mutually different detection directions.

8. The sensor device according to claim 7, wherein the detection directions of the two sensors are orthogonal.

9. The sensor device according to claim 1, wherein the base member and the exterior member are integrally formed.

10. The sensor device according to claim 1,
wherein the base member comes into line contact or point contact with the fitting member.

11. The sensor device according to claim 1,
wherein the fitting member has a shape capable of holding a shaft-shaped portion of the hitting tool, and
wherein the base member is mounted on the fitting member.

12. The sensor device according to claim 1,
wherein the fitting member and the base member have mutually corresponding shapes capable of holding a shaft-shaped portion of the hitting tool, and
wherein the base member is fitted on the hitting tool by holding the shaft-shaped portion between the base member and the fitting member.

* * * * *